United States Patent
Moore

(10) Patent No.: US 8,193,347 B2
(45) Date of Patent: Jun. 5, 2012

(54) METAL COMPLEXES OF TETRAAZAMACROCYCLE DERIVATIVES

(75) Inventor: Dennis A. Moore, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 704 days.

(21) Appl. No.: 12/282,399

(22) PCT Filed: Mar. 14, 2007

(86) PCT No.: PCT/US2007/006514
§ 371 (c)(1),
(2), (4) Date: Sep. 10, 2008

(87) PCT Pub. No.: WO2007/106546
PCT Pub. Date: Sep. 20, 2007

(65) Prior Publication Data
US 2009/0036674 A1   Feb. 5, 2009

Related U.S. Application Data

(60) Provisional application No. 60/782,093, filed on Mar. 14, 2006.

(51) Int. Cl.
*C07D 225/00* (2006.01)
*C07D 257/02* (2006.01)
(52) U.S. Cl. ...................... 540/465; 540/474
(58) Field of Classification Search ........................ None
See application file for complete search history.

(56) References Cited

U.S. PATENT DOCUMENTS

| | | |
|---|---|---|
| 4,877,600 A | 10/1989 | Bonnemain et al. |
| 4,885,363 A | 12/1989 | Tweedle et al. |
| 5,994,536 A | 11/1999 | Petrov et al. |
| 6,156,890 A | 12/2000 | Platzek et al. |
| 6,576,222 B2 | 6/2003 | Platzek et al. |
| 6,867,298 B2 | 3/2005 | Buchwald et al. |

FOREIGN PATENT DOCUMENTS

| | | |
|---|---|---|
| EP | 0 872 479 | 10/1998 |
| WO | WO 94/27498 | 12/1994 |
| WO | WO 98/55467 | 12/1998 |
| WO | WO 00/30688 | 6/2000 |
| WO | WO 02/48119 | 6/2002 |
| WO | WO 2007/064661 | 6/2007 |

OTHER PUBLICATIONS

Brunner et al., "$Cu^{2+}$ complexes of tetraazacyclododecanes functionalized with benzyl side chains carrying carboxylic or phenolic groups", Supramolecular Chemistry, 1992, vol. 2, pp. 103-110, XP 000572096.

Kruper, Jr. et al., "Unexpected Selectivity in the Alkylation of Polyazamacrocycles", J. Org. Chem., 1993, 58, pp. 3869-3876.

Pope et al., "Design, synthesis and photophysical studies of an emissive, europium based, sensor for zinc", Dalton Trans., 2006, pp. 3108-3113, XP 002446469.

Quici et al., "Highly homogeneous, transparent and luminescent $SiO_2$ glassy layers containing a covalently bound tetraazacyclododecane-triacetic acid-Eu(III)-acetophenone complex", J. Mater. Chem., 2006, 16, pp. 741-747, XP002446468.

Ranaganathan et al., "Polymethylated DOTA Ligands. 1. Synthesis of Rigidified Ligands and Studies on the Effects of Alkyl substitution on Acid-Base Properties and Conformational Mobility", Inorganic Chemistry, 2002, vol. 41, No. 25, pp. 68466855.

*Primary Examiner* — Noble Jarrell

(57) ABSTRACT

Improved methods for synthesizing bifunctional chelates of tetraazamacrocycle derivatives and intermediates thereof are disclosed as well as novel tetraazamacrocycle derivatives and intermediates thereof.

8 Claims, 16 Drawing Sheets

Sodium tert-butyl 2,2',2''-(10-
(cyanomethyl)-1,4,7,10-
tetraazacyclododecane-
1,4,7-triyl)triacetate bromide

Compound IX

METAL COMPLEXES OF TETRAAZAMACROCYCLE DERIVATIVES

CROSS REFERENCE TO RELATED APPLICATIONS

This application is a national stage application of PCT/US20071006514, filed Mar. 14, 2007, which claims the benefit of U.S. application Ser. No. 60/782,093, filed Mar. 14, 2006.

FIELD OF THE INVENTION

The present invention relates generally to synthesis of bifunctional chelates of tetraazamacrocycle derivatives and intermediates thereof.

BACKGROUND

The tetraazamacrocycles are well-known platforms for generating ligand systems for coordinating metal ions and the N-carboxyalkyl and N-phosphonoalkyl derivatives are popular in inorganic chemistry for forming some of the most stable metal complexes. This class of ligands plays an important role in several industrial and biomedical processes where metal chelation is desired. For example, derivatives such as 1,4,7,10-tetraazacyclo-dodecane-1,4,7,10-tetracetic acid (DOTA) and 1,4,7,10-tetraazacyclo-dodecane-1,4,7,10-tetramethylene-phosphonic acid (DOTP) have wide applicability in demetallation of water and other fluid systems in industry. Further, the metal complexes have recently been found useful in both imaging and therapeutic applications whereby otherwise toxic metal ions are rendered safe by complexing with these ligands. See, for example, A E Martell and R D Hancock, "Metal Complexes in Aqueous Solutions", Springer Verlag, 1996, chapter 5.

In medicine, the polyazamacrocyclic ligands have been widely used as chelators for a variety of transition metals. The macrocyclic polyaminocarboxylates such as DOTA and 1,4,8,11-tetraazacyclo-tetradecane-1,4,8,11-tetracetic acid (TETA) are known to form highly stable metal complexes due to their highly preorganized macrocyclic ligand framework. The macrocyclic ligands can form complexes with radionuclides such as Tc-99m, In-111, Ga-67, Y-90, Re-188, Sm-153 or other radioactive metal ions to yield pharmaceuticals useful in radionuclide imaging and therapy. The ligands can form complexes with metal ions heavier than iodine to generate products useful in X-ray imaging. Further, the ligands can bind paramagnetic metal ions such as $Gd^{+3}$, $Mn^{+2}$, $Fe^{+3}$, $Cr^{+3}$ to yield magnetic resonance imaging (MRI) agents. In special cases, the macrocycles can be specially modified so as to both bind a metal ion and then deliver the metal complex compounds to specific targets for improved imaging or targeted therapy. Such dual function ligands are often referred to as bifunctional ligands.

Cyclen, 1,4,7,10-tetraazacyclododecane, is the scaffold commonly used for generating DOTA, a key ligand for formation of metal complexes hereinbefore described. Cyclen is particularly useful for generating the triscarboxymethylated DO3A, 4,7,10-triscarboxymethyl-1,4,7,10-tetraazacyclododecane, a ligand by itself and also a key intermediate which can be variously derivatized at the free macrocyclic nitrogen for formation of a range of bifunctional ligands, the metal complexes of which are useful for imaging and therapy. For example, in U.S. Pat. No. 4,877,600, Bonnemain et al. disclosed the gadolinium complex of DOTA for imaging/MRI. In U.S. Pat. No. 4,885,363, Tweedle et al. similarly disclosed a gadolinium complex of DO3A-HP, a DO3A-derivative in which the free macrocyclic N was alkylated with 2-hydroxypropyl, for imaging. Similarly, in U.S. Pat. No. 5,994,536, Petrov et al. disclosed another gadolinium complex for MRI, Gd-DO3A-butriol in which the alkyl substituent at the free macrocyclic N is 2,3-dihydroxy-1-(hydroxymethyl)propyl. Others have disclosed other targetable DO3A-derivatives; see, e.g., Platzek et al., U.S. Pat. No. 6,576,222.

Typically, precursors of bifunctional chelates are synthesized by alkylation of an esterified DO3A, such as DO3A tris(t-butyl ester), in a strong base, such as an alkali metal hydroxide or an alkali metal carbonate. For example, in U.S. Pat. No. 6,576,222 Platzek et al. disclosed alkylation of DO3A in 6N potassium hydroxide (KOH). In U.S. Pat. No. 4,885,363, Tweedle et al. similarly disclosed N-alkylations of DO3A in excesses of sodium hydroxide (NaOH) or potassium carbonate ($K_2CO_3$). Platzek et al. and Tweedle et al. then isolated the macrocycle as a free base by filtration and/or chromatography, providing low yields and/or oils that are hard to handle for subsequent reactions. Alternatively, cyclen may be monoalkylated first with a unique group of interest, for example a bifunctional targeting group or a linker, and then derivatized at the other three nitrogen atoms to produce a DO3A-type moiety. See for example, Kruper et al., J. Org. Chem., 1993, 58, 3869-3875, In the process described by Kruper et al., an HBr salt of the monoalkylated macrocycle was generated which required additional purification by chromatography, hence lowering their yield.

SUMMARY

Among the various aspects of the present invention is an improved synthetic pathway for the facile generation of tetraazamacrocycle(s).

Briefly, one aspect of the present invention is a process for alkylating the free macrocyclic nitrogen of a tris-N-substituted tetraazamacrocycle (1) to yield a tetra-N-substituted tetraazamacrocycle (2) in the presence of a weak base. The tris-N-substituted tetraazamacrocycle (1) and tetra-N-substituted tetraazamacrocycle (2) have the formulae:

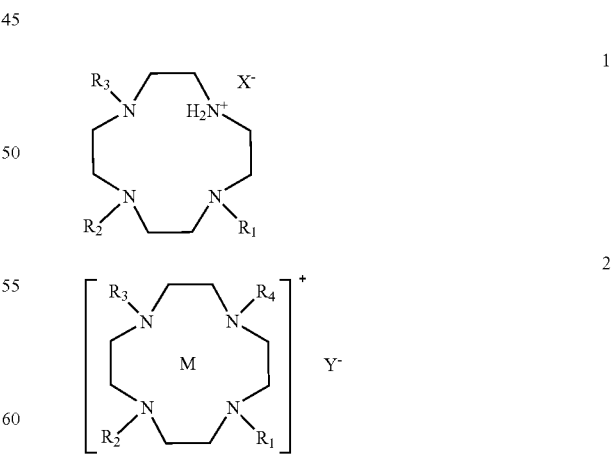

wherein M is a metal ion; $R_1$, $R_2$ and $R_3$ are independently hydrocarbyl, substituted hydrocarbyl, or heterocyclo, $R_4$ is optionally substituted alkyl or aryl, X is a counterion; and Y is a leaving group.

In another aspect, a compound of Formula 3 is provided,

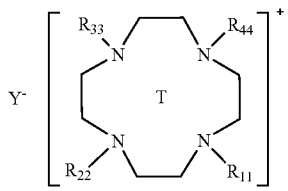

wherein T is a metal ion selected from the group consisting of alkali metals, alkaline earth metals, and transition metals bearing (+1) or (+2) charges; $R_{11}$, $R_{22}$ and $R_{33}$ are independently selected from the group consisting of —$CH_2CO_2R_5$, —$CH_2ArOR_5$, —$CH_2SR_5$, —$CH_2PO_3H_2$, $CH_2SO_3H$, —$CH_2Ar(OR_5)_2$, —$CH_2Ar(OR_5)R_5$ and —$CH_2Ar(OR_5)_2R_6$; $R_{44}$ is —$CH_2ArOR_7$, —$CH(R_8)CO_2R_7$, —$CH_2Ar(OR_7)_2$—$CH_2Ar(OR_7)R_8$, or —$CH_2Ar(OR_7)_2R_8$; $R_5$, $R_6$ and $R_7$ are independently H, alkyl or substituted alkyl; $R_8$ is selected from a group consisting of optionally substituted acyl, aryl and heteroaryl, alkoxy, hydroxy, halo, amino, nitro, thiols, disulfides, carbohydrates, vitamins, combinations and derivatives; Ar is an optionally substituted phenyl, pyrimidinyl or pyridinyl; and Y is a counter ion selected from the group consisting of the halides, methanesulfonate, trifluoroacetate, trifluormethanesulfonate and p-toluenesulfonate.

Another aspects of the present invention are certain tetra-N-substituted tetraazamacrocycles (2) which may be produced in this reaction. These products are useful intermediates for generating bifunctional chelates for imaging and treatment of diseased tissues.

Other objects and features of this invention will be in part apparent and in part pointed out hereinafter.

DETAILED DESCRIPTION

Figure 1:
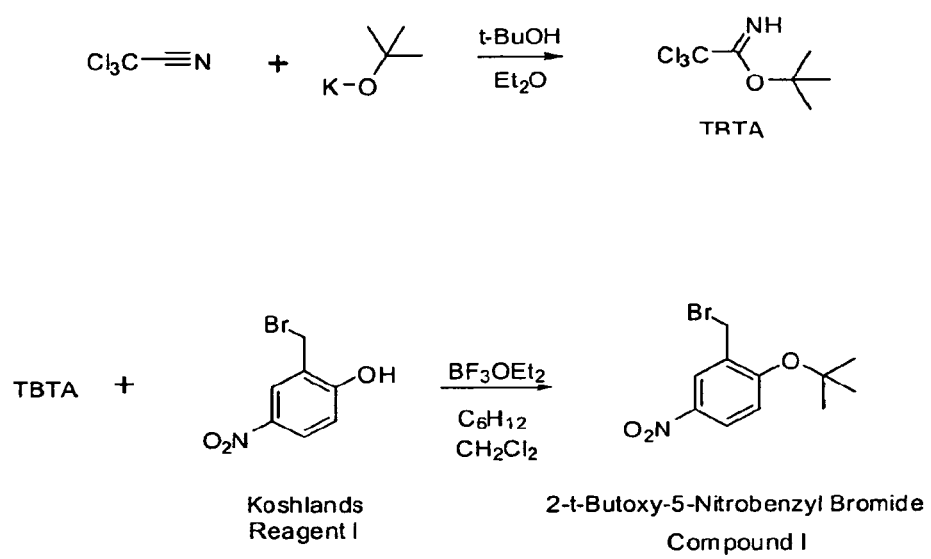
FIG. 1 is an illustration of a reaction synthesis of 2-t-butoxy-5-nitrobenzyl bromide.

In one embodiment, the present invention is directed to a process for the alkylation of trisubstituted tetraazamacrocyles, 1, to yield a tetrasubstituted product, 2. The process comprises alkylating the free macrocyclic nitrogen atom of macrocylcle 1 with an alkylating agent, $R_4Y$, in an organic solvent in the presence of a weak base, where the trisubstituted macrocycle, 1, and tetrasubstitututed product, 2, have the general structures:

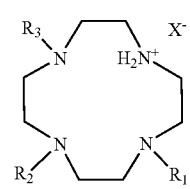

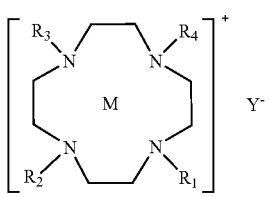

wherein, M is a metal ion; $R_1$, $R_2$ and $R_3$ are independently hydrocarbyl, substituted hydrocarbyl or heterocyclo; $R_4$ is optionally substituted, alkyl or aryl, X is a counterion; and Y is a leaving group.

M is derived from the metal ion component of the weak base used in the conversion of (1) to (2). Typically, M is selected from alkali metals, alkaline earth metals, transition metals and the lanthanides. In one embodiment, M is an alkali metal ion. In another embodiment, M is sodium.

Depending on the intended application, $R_1$, $R_2$ and $R_3$ may provide a source of metal binding entities. Alternatively, they may independently or collectively, also function in targeting (directing the macrocyclic complex to a predetermined site) or as linkers to other molecules (for generating larger molecular aggregates). In one embodiment, $R_1$, $R_2$ and $R_3$ are independently hydrocarbyl, substituted hydrocarbyl or heterocyclo. They may be independently selected from the group consisting of optionally substituted hydrocarbyls, heterosubstituted hydrocarbyls and heterocycles. For example, $R_1$, $R_2$ and $R_3$ may independently be alkyl, alkenyl, alkynyl, aryl or heterocyclyl, optionally substituted with acyl, amino, hydroxy, alkoxy, aryloxy, thio, nitro, or combinations thereof. In one embodiment, $R_1$, $R_2$ and $R_3$ are the same and are hydrocarbyl, substituted hydrocarbyl or heterocyclo. In another embodiment, $R_1$, $R_2$ and $R_3$ are not the same and are independently selected from the group consisting of —$CH_2CO_2R_5$, —$CH_2ArOR_5$, —$CH_2SR_5$, —$CH_2PO_3H_2$, $CH_2SO_3H$, —$CH_2Ar(OR_5)_2$, —$CH_2Ar(OR_5)R_6$ and —$CH_2Ar(OR_5)_2R_6$, wherein $R_5$ and $R_6$ are independently hydrogen, alkyl, or substituted alkyl. For example, in this embodiment, $R_5$ and $R_6$ may be independently selected from H, t-Bu, Et, Me, methoxybenzyl, or benzyl. In one particular embodiment, $R_1$, $R_2$ and $R_3$ are each —$CH_2CO_2R_5$ wherein $R_5$ is t-butyl. In an alternative described above, $R_1$, $R_2$ and $R_3$ may also provide targeting and linking groups. In this case, $R_1$, $R_2$ and $R_3$ are independently selected from the group consisting of —$CH_2CO_2R_5$, —$CH_2ArOR_5$, —$CH_2SR_5$, —$CH_2Ar(OR_5)_2$, —$CH_2Ar(OR_5)R_6$ and —$CH_2Ar(OR_5)_2R_6$, wherein $R_5$ and $R_6$ independently comprise acyl, optionally substituted aryl and heteroaryl, alkoxy, hydroxy, halo, amino, nitro, thiols, disulfides, carbohydrates, vitamins and combinations and derivatives thereof.

In general, $R_4$ is a group with a potential for targeting, i.e., directing the macrocyclic derivative to a target of interest. However, $R_4$ may also be a source of metal binding entity and may serve the role of linking the macrocyclic derivative with other molecules for a wide range of applications. In one embodiment, $R_4$ is an optionally substituted alkyl or aryl, acyl or combinations thereof. In a preferred embodiment, $R_4$ is —$CH_2ArOR_7$, —$CH(R_8)CO_2R_7$, —$CH_2Ar(OR_7)_2$, —$CH_2Ar(OR_7)R_8$, or —$CH_2Ar(OR_7)_2R_8$, wherein (i) Ar is an optionally substituted phenyl, pyrimidinyl or pyridinyl, (ii) $R_7$ is hydrogen or an alkyl, such as t-Bu, Et, Me, methoxybenzyl, or benzyl and (iii) $R_8$ is selected from the group consisting of acyl, optionally substituted aryl and heteroaryl, alkoxy, hydroxy, halo, amino, nitro, thiols, disulfides, carbohydrates, vitamins and combinations and derivatives thereof.

X is the counterion of the acid salt of the trisubstituted macrocyclic substrate, 1 and X is eliminated when the substrate is converted to the free base prior to alkylation. Typically, X is a halide, nitrate, sulfate or phosphate. In one embodiment, X is a halide ion.

The alkylating agents used in the process of the present invention have the formula $R_4Y$. $R_4$ is the substituent introduced onto the macrocyclic nitrogen and has been described in detail above. Typically, $R_4$ may be the source of targeting groups or linking moieties. Y is a leaving group in the alkylation reaction and is described below.

In one embodiment Y is a leaving group selected from the group consisting of halide, methanesulfonate, trifluoroacetate, p-toluenesulfonate and trifluormethanesulfonate ions. Preferably, Y comprises bromide, chloride, iodide, methanesulfonate, trifluoroacetate, trifluormethanesulfonate or p-toluenesulfonate. Of the leaving groups, Y, bromide is typically preferred.

One embodiment of the present invention is directed to a process wherein, (i) $R_1$, $R_2$ and $R_3$ are independently selected from the group consisting of —$CH_2CO_2R_5$, —$CH_2ArOR_5$, —$CH_2SR_5$, —$CH_2PO_3H_2$, $CH_2SO_3H$, —$CH_2Ar(OR_5)_2$, —$CH_2Ar(OR_5)R_6$ and —$CH_2Ar(OR_5)_2R_6$, and (ii) $R_4$ is —$CH_2ArOR_7$, —$CH(R_8)CO_2R_7$, —$CH_2Ar(OR_5)_2$—$CH_2Ar(OR_7)R_8$, or —$CH_2Ar(OR_7)_2R_8$. In this embodiment, Ar is an optionally substituted phenyl, pyrimidinyl or pyridinyl, $R_5$, $R_6$ and $R_7$ are independently H, an alkyl such as t-Bu, Et or Me, methoxybenzyl, or benzyl, $R_8$ is selected from the group consisting of acyl, optionally substituted aryl and heteroaryl, alkoxy, hydroxy, halo, amino, nitro, thiols, disulfides, carbohydrates, vitamins, combinations and derivatives, and Y is selected from the group consisting of bromide, chloride, iodide, methanesulfonate, trifluoroacetate, trifluormethanesulfonate and p-toluenesulfonate. For example, in this embodiment, $R_1$, $R_2$ and $R_3$ may be —$CH_2CO_2R_5$ wherein each $R_5$ is independently hydrogen or alkyl such as t-Bu, Et or Me. In another aspect of this embodiment, Ar is phenyl, M is sodium, $R_5$ is t-butyl and Y is bromide.

In another embodiment, (i) Ar is an optionally substituted phenyl, pyrimidinyl or pyridinyl, (ii) $R_1$, $R_2$ and $R_3$ are independently selected from the group consisting of —$CH_2CO_2R_5$, —$CH_2ArOR_5$, —$CH_2SR_5$, —$CH_2PO_3H_2$, $CH_2SO_3H$, —$CH_2Ar(OR_5)_2$, —$CH_2Ar(OR_5)R_6$ and —$CH_2Ar(OR_5)_2R_6$, (iii) $R_4$ is —$CH_2Ar(OR_5)NO_2$ or —$CH(CO_2R_5)(CH_2)_4NH(CO_2CH_2Ar)$, (iv) $R_5$ and $R_6$ are independently H, t-Bu, Et, Me, methoxybenzyl, or benzyl, and (v) Y is a leaving group comprising bromide, chloride, iodide, methanesulfonate, trifluoroacetate, trifluormethanesulfonate or p-toluenesulfonate. For example, in this embodiment, Ar is phenyl, M is sodium, $R_5$ is t-butyl, and Y is bromide.

In an alternative embodiment, $R_1$, $R_2$ and $R_3$ are independently —$CH_2CO_2R_5$ and $R_4$ is —$CH_2Ar(OR_5)NO_2$ or —$CH(CO_2R_5)(CH_2)_4NH(CO_2)CH_2Ar$. For example, in this embodiment, Ar is phenyl, M is sodium, $R_5$ is t-butyl, and Y is bromide.

The weak base primarily renders the trisubstituted macrocycle basic and also scavenges the acidic byproduct of the reaction. Typically, the weak base is a base having a $pK_b$ of about 12 or less. In one embodiment, the weak base has a $pK_b$ not in excess of 11. In another embodiment, the weak base has a $pK_b$ of about 10 or less. In one preferred embodiment, the weak base is a metal salt of a bicarbonate, biphosphate, bisulfate, acetate or citrate, or a combination thereof. In another embodiment of the invention, the weak base comprises bicarbonate salts of alkali metals, alkaline earth metals, transition metals or the lanthanide metals. In one embodiment, alkali metal bicarbonates are the weak bases of choice. In another embodiment, the weak base is sodium bicarbonate.

The amount of weak base employed in carrying out the reaction of the invention is significantly reduced to a range close to about 1:1 in molar ratio of macrocyclic substrate to base; higher amounts of base may hinder the yield. In one embodiment, the amount of weak base employed in carrying out the reaction of the invention will normally be in the molar ratio range of from about 1:0.9 to about 1:1.2. In another embodiment, the ratio of substrate to base is from about 1:1 to about 1:1.1. In yet another embodiment, the ratio 1:1.

The organic solvent for the alkylation process may be, for example a polar, aprotic solvent. In one embodiment, the solvent comprises acetonitrile, dimethylformamide (DMF), tetrahydrofuran (THF), dimethylacetamide (DMAC) or 1,2-dimethoxyethane (DME). In another embodiment, the organic solvent is acetonitrile.

Reaction conditions such as temperature and duration can be varied so as to maximize the yield of the product (2). Typically, the temperature is chosen to drive the reaction to completion in a reasonable time. For example, a temperature range of about 30° C. to about 35° C. will typically permit completion of the alkylation overnight. Less reactive reactants will benefit from a higher temperature range if the reaction is to proceed to completion overnight. Contrarily, if the substrates are more reactive, then a lower temperature or a shorter duration may be preferred. In one embodiment of the invention, the temperature of the reaction is from about 25° C. to about 40° C. and the reaction is allowed to stir overnight. In another embodiment, the temperature is from about 30° C. to about 35° C.

The foregoing recitation of specific compounds and mixtures can be used in formulating the composition of the present invention, as can salts, esters, or other derivatives. The process of the present invention can be used to prepare a large array of compounds.

The process of the present invention is used to prepare a compound corresponding to structure 3 as metal salts which may be conveniently isolated from the reaction medium quantitatively, in high yields, without need of further chromatography. The compounds corresponding to structure 3 are useful intermediates for generating bifunctional chelates. In one embodiment, the compounds correspond to the structure:

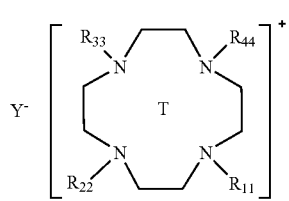

3 wherein T is a metal ion selected from the group consisting of alkali metals, alkaline earth metals or transition metals with (+1) or (+2) charges; $R_{11}$, $R_{22}$ and $R_{33}$ are independently hydrocarbyl, substituted hydrocarbyl or heterocyclo; $R_{44}$ is optionally substituted alkyl or aryl, or combinations thereof; and Y is a counter ion selected from the group consisting of bromide, chloride, iodide, methanesulfonate, trifluoroacetate, trifluormethanesulfonate and p-toluenesulfonate ions.

In one embodiment, $R_{11}$, $R_{22}$ and $R_{33}$ are independently acyl, hydrocarbyl, substituted hydrocarbyl or heterocyclo. They may be independently selected from the group consisting of optionally substituted hydrocarbyls, heterosubstituted hydrocarbyls and heterocycles. For example, $R_{11}$, $R_{22}$ and $R_{33}$ may independently be alkyl, alkenyl, alkynyl, aryl or heterocyclyl, optionally substituted with acyl, amino, hydroxy, alkoxy, aryloxy, thio, nitro, or combinations thereof.

In one embodiment, $R_{11}$, $R_{22}$ and $R_{33}$ are the same and are, hydrocarbyl, substituted hydrocarbyl or heterocyclo. In another embodiment, $R_{11}$, $R_{22}$ and $R_{33}$ are not the same and are independently selected from the group consisting of —$CH_2CO_2R_5$, —$CH_2ArOR_5$, —$CH_2SR_5$, —$CH_2PO_3H_2$, $CH_2SO_3H$, —$CH_2Ar(OR_5)_2$, —$CH_2Ar(OR_5)R_6$ and —$CH_2Ar(OR_5)_2R_6$, wherein $R_5$ and $R_6$ are independently alkyl or substituted alkyl. For example, in this embodiment, $R_5$ and $R_6$ may independently be H, t-Bu, Et, Me, methoxybenzyl, or benzyl. In another example of this embodiment, $R_1$, $R_2$ and $R_3$ are each —$CH_2CO_2R_5$ wherein $R_5$ is t-butyl.

In one embodiment, $R_{44}$ is acyl, an optionally substituted alkyl or aryl, or combinations thereof. In a preferred embodiment, $R_{44}$ is —$CH_2ArOR_7$, —$CH(R_8)CO_2R_7$, —$CH_2Ar(OR_7)_2$—$CH_2Ar(OR_7)R_8$, or —$CH_2Ar(OR_7)_2R_8$, wherein (i) Ar is an optionally substituted phenyl, pyrimidinyl or pyridinyl, (ii) $R_7$ is hydrogen or an alkyl, such as t-Bu, Et or Me and (ii) $R_8$ is selected from the group consisting of acyl, optionally substituted aryl and heteroaryl, alkoxy, hydroxy, halo, amino, nitro, thiols, disulfides, carbohydrates, vitamins and combinations and derivatives thereof. In an alternative embodiment, $R_{44}$ is —$CH_2Ar(OR_5)NO_2$ or —$CH(CO_2R_5)(CH_2)_4NH(CO_2)CH_2Ar$. In a preferred embodiment, and Ar is phenyl, $R_{44}$ is —$CH_2Ar(OR_5)NO_2$ or —$CH(CO_2R_5)(CH_2)_4NH(CO_2)CH_2Ar$ and $R_5$ is t-butyl.

In one embodiment Y is selected from the group consisting of halide, methanesulfonate, trifluoroacetate, p-toluenesulfonate and trifluormethanesulfonate ions. Preferably, Y comprises bromide, chloride, iodide, methanesulfonate, trifluoroacetate, trifluormethanesulfonate or p-toluenesulfonate. Of the leaving groups Y, bromide is typically preferred.

In another embodiment, (i) $R_{11}$, $R_{22}$ and $R_{33}$ are independently selected from the group consisting of —$CH_2CO_2R_5$, —$CH_2ArOR_5$, —$CH_2SR_5$, —$CH_2PO_3H_2$, $CH_2SO_3H$, —$CH_2Ar(OR_5)_2$, —$CH_2Ar(OR_5)R_6$ and —$CH_2Ar(OR_5)_2R_6$, (ii) $R_{44}$ is —$CH_2Ar(OR_5)NO_2$ or —$CH(CO_2R_5)(CH_2)_4NH(CO_2CH_2Ar)$, (iii) $R_5$ and $R_6$ are independently H, t-Bu, Et, Me, methoxybenzyl or benzyl, (iv) Ar is an optionally substituted phenyl, pyrimidinyl or pyridinyl, and (v) Y is a leaving group comprising bromide, chloride, iodide, methanesulfonate, trifluoroacetate, trifluormethanesulfonate or p-toluenesulfonate. In a preferred embodiment, Ar is phenyl, T is sodium; $R_5$ is t-butyl; and Y is bromide.

In an alternative embodiment, $R_{11}$, $R_{22}$ and $R_{33}$ are independently —$CH_2CO_2R_5$ and $R_4$ is —$CH_2Ar(OR_5)NO_2$ or —$CH(CO_2R_5)(CH_2)_4NH(CO_2)CH_2Ar$. For example, in this embodiment, T is sodium, $R_5$ is t-butyl; Ar is phenyl and Y is bromide.

In one embodiment, the invention is directed to a compound corresponding to the structure:

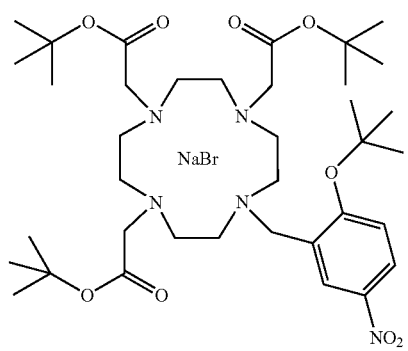

1,4,7,10-Tetraazacyclododecane-1,4,7-triacetic acid, 10-[(2-t-butoxy-5-nitrophenyl)methyl]-tri-t-butyl ester, sodium bromide complex In another embodiment, invention is directed to a compound corresponding to the structure:

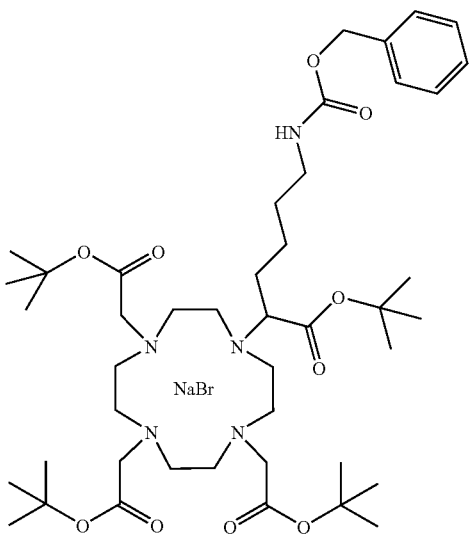

2-{[2',2'',2'''-(1,4,7,10-Tetraaza-cyclododecane-1,4,7-triyl)triacetic acid]-10-yl}-6-[(benzyloxycarbonyl)-amino]hexanoic acid, tetra-t-butyl

DEFINITIONS

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "counterion" as used herein alone or as part of another group refers to an ion that exists in the formulation for the purpose of maintaining electrical neutrality of the compound. Counterions may be positive or negative.

The terms "halogen", "halide" or "halo" as used herein alone or as part of another group refer to chlorine, bromine, fluorine, and iodine.

The term "heteroatom" shall mean atoms other than carbon and hydrogen. The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably contain 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "leaving group" in an N-alkylation of a tetraazamacrocyle refers to the component of the alkylating agent which is not substituted onto the macrocyclic nitrogen atom. These typically comprise halide ions, methanesulfonate, trifluoroacetate, trifluoromethanesulfonate or p-toluenesulfonate.

The term "weak base" refers to a base which does not completely dissociate when in solution. Typically, it is the conjugate base of a weak acid.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "protecting group" as used herein denote a group capable of protecting reactive group, e.g., a free hydroxyl group ("protected hydroxyl"), amine group ("protected amine"), sulfhydryl group ("protected sulfhydyl") etc., which, subsequent to the reaction for which protection is employed, may be removed without disturbing the remainder of the molecule. A variety of protecting groups and the synthesis thereof may be found in "Protective Groups in Organic Synthesis" by T. W. Greene, John Wiley and Sons, 1981, or Fieser & Fieser.

The following examples illustrate specific embodiments of the invention. As would be apparent to skilled artisans, various changes and modifications are possible and are contemplated within the scope of the invention described.

EXAMPLE 1

Preparation of 1,4,7,10-Tetraazacyclododecane-1,4, 7-triacetic acid, 10-[(2-t-butoxy-5-nitrophenyl)methyl], tri-t-butyl ester, Compound III t-Butyl trichloroacetimidate (TBTA): Potassium t-butoxide (1M in t-butanol), 69 mL (0.069 mole), was dissolved in diethyl ether, 69 mL. This solution was added dropwise, over 30 minutes, to a cold, 0° C., solution of trichloroacetonitrile, 100 g (0.69 mole), in diethyl ether, 69 mL. The mixture was allowed to warm to room temperature over one hour, and was then stirred for an additional hour with heating at reflux. The mixture was cooled to room temperature and evaporated under reduced pressure to yield an oil. The oil was dissolved in hexanes, 140 mL, and filtered to remove potassium salts. The filtrate was evaporated under reduced pressure and the residue was vacuum distilled. The fraction distilling at 2.4 mm Hg and 40° C. was collected. The yield was 105 g, 69% based on trichloroacetonitrile. $^1$H nmr (300 MHz CDCl$_3$) δ (ppm): 1.58, (s, 9H), 8.21 (br, s, 1H). $^{13}$C (75.45 MHz, CDCl$_3$) δ (ppm): 27.23, 83.86, 92.78, 160.33. (Armstrong et al.)

2-t-butoxy-5-nitrobenzyl bromide, Compound I: The synthesis of 2-t-butoxy-5-nitrobenzyl bromide, Compound I, is illustrated in FIG. 1. A suspension of 2-hydroxy-5-nitrobenzyl-bromide, 19.4 g (0.0836 mole), cyclohexane, 334 mL, and dichloromethane, 167 mL, was stirred under nitrogen. To this was added a solution of t-butyl trichloroacetimidate, 73.08 g (0.334 mole), in cyclohexane, 669 mL, dropwise over 3.5 hours. The mixture was stirred for one hour after completion of the addition and boron trifluoride etherate, 200 μL, was added. The mixture was allowed to stir overnight. A large amount of precipitate, trichloroacetamide, formed. The reaction mixture was treated with sodium bicarbonate, 4.00 g (0.0418 mole), stirred for one hour and filtered. The solids were washed with diethyl ether and the combined filtrates concentrated to an oil under reduced pressure. The oil was treated with hexanes, 100 mL, and the solution stirred until crystals formed. After cooling to −20° C. and stirring for an additional hour, the resulting solid was collected by filtration, washed with cold, fresh hexane, suctioned dry and vacuum dried. The yield was 13.2 g, 55% based on 2-hydroxy-5-nitrobenzyl bromide. Calc C, 45.85; H, 4.90; N, 4.86; Br, 27.73. Found C, 45.39; H, 5.07; N, 4.94; Br, 27.66. $^1$H nmr (300 MHz CDCl$_3$) δ (ppm): 1.58 (s, 9H), 4.48 (s, 2H), 7.10 (d, JH=9 Hz, 1H), 8.11 (dd, J=9 Hz, J=2.7 Hz, 1H), 8.22 (d, J=2.7 Hz, 1H). $^{13}$C (75.45 MHz, CDCl$_3$) δ (ppm): 28.92, 81.59, 116.86, 125.07, 126.34, 129.98, 140.69, 159.97.

Figure 2:
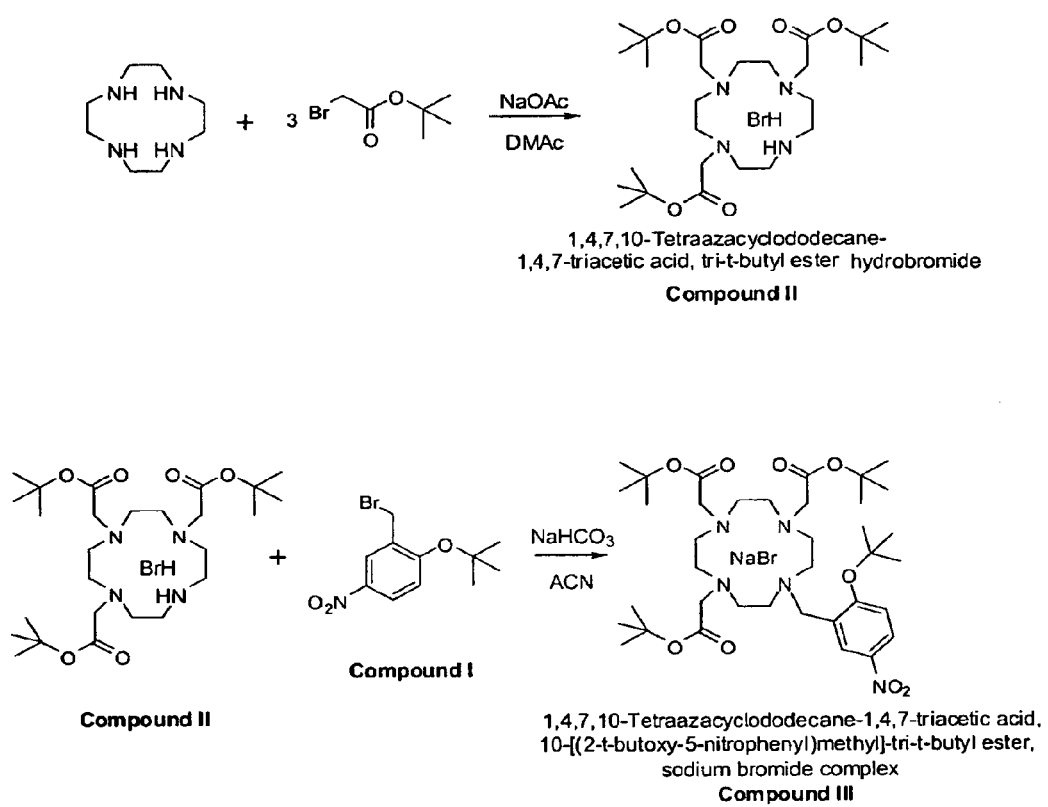
FIG. 2 is an illustration of a reaction synthesis of 1,4,7,10-Tetraazacyclododecane-1,4,7-triacetic acid, tri-t-butyl ester Hydrobromide, Compound II, and 1,4,7,10-Tetraazacyclododecane-1,4,7-triacetic acid, 10-[(2-t-butoxy-5-nitrophenyl)methyl]-, tri-t-butyl ester, Compound III.

The synthesis of 1,4,7,10-Tetraazacyclododecane-1,4,7-triacetic acid, tri-t-butyl ester Hydrobromide, Compound II, and 1,4,7,10-Tetraazacyclododecane-1,4,7-triacetic acid, 10-[(2-t-butoxy-5-nitrophenyl)methyl]-, tri-t-butyl ester, Compound III, is illustrated in FIG. 2.

1,4,7,10-Tetraazacyclododecane-1,4,7-triacetic acid, tri-t-butyl ester Hydrobromide, Compound II: Cyclen, 32.0 g (0.186 mole), and sodium acetate trihydrate, 75.8 g (0.557 mole), were stirred with dimethylacetamide, 600 mL, for one hour. To this mixture was added dropwise, a solution of t-butyl bromoacetate, 109 g (0.557 mole), in 150 mL dimethylacetamide, over four hours. The rate of the addition was adjusted so as to keep the temperature of the reaction mixture less than 25° C. The mixture was allowed to stir over two nights. After cooling to −10° C. and stirring for two hours, the resulting solid was collected by filtration, washed with cold, fresh dimethylacetamide, 50 mL, and dried by suction. The solid was dissolved in chloroform, 0.5 L, and the solution washed with water, 3×200 mL. The organic phase was collected, dried with magnesium sulfate, filtered and concentrated under reduced pressure to 300 mL. Hexanes, 300 mL, was added and the solution stirred for one hour at room temperature; crystallization began after a few minutes. The resulting slurry was cooled to −20° C., stirred for two hours and filtered. The solid was washed with cold, fresh chloroform-hexanes, 50 mL (1:1), solvent was removed by suction and the solid was vacuum dried overnight at room temperature. The yield was 69 g, (62% based on cyclen). $^1$H nmr (300 MHz, CDCl$_3$) δ (ppm): 1.44 (s, 9H), 1.45 (s, 18H), 2.87-2.90 (br, m, 12H), 3.07-3.08 (br, m, 4H), 3.27 (s, 2H), 3.56 (s, 4H), 9.97 (br, s, 2H). $^{13}$C nmr (75.45 MHz, CDCl$_3$) δ (ppm): 28.15, 28.18, 47.44, 48.68, 49.11, 51.15, 51.25, 58.11, 81.54, 81.70, 169.32, 170.21. (Himmelsbach et al.)

1,4,7,10-Tetraazacyclododecane-1,4,7-triacetic acid, 10-[(2-t-butoxy-5-nitrophenyl)-methyl]-, tri-t-butyl ester, sodium bromide complex, Compound III: 1,4,7,10-Tetraazacyclo-dodecane-1,4,7-triacetic acid, tri-t-butyl ester hydrobromide, 8.46 g (0.0142 mole), was stirred with aqueous sodium hydroxide, 0.1N 200 mL, and diethyl ether, 200 mL. When the entire solid had dissolved, the organic phase was collected and the aqueous phase washed with diethyl ether, 2×200 mL. The combined organic extracts were dried with magnesium sulfate, filtered and evaporated, under reduced pressure, to an oil. The oil was dissolved in acetonitrile, 135 mL. To this solution was added sodium bicarbonate, 1.19 g (0.0142 mole), followed by 2-t-butoxy-5-nitrobenzyl bromide, 4.50 g (0.0156 mole). The mixture was warmed to 35° C., and stirred overnight under argon. When the reaction was complete by nmr, after 12-14 hours total time, the mixture was filtered and the filtrate was concentrated under reduced pressure to give an oil. The oil was suspended in diethyl ether, 50 mL, and a white precipitate formed after stirring. The solid was collected by filtration, suctioned dry and dried in a vacuum overnight. The yield was 11.7 g, 98% based on starting 1,4,7,10-Tetraazacyclododecane-1,4,7-triacetic acid, tri-t-butyl ester hydrobromide. Anal. Calc. C, 52.73; H, 7.77; N, 8.31; Br, 9.48. Found C, 52.31; H, 7.68; N, 8.26; Br, 9.67. $^1$H nmr (300 MHz, CDCl$_3$) δ (ppm): 1.45 (s, 27H), 1.51 (s, 9H), 1.78 (br, s, 2H), 2.20 (m, 4H), 2.33 (br, 4H), 2.73 (br, 4H), 2.93 (complex, br, 6H), 3.10 (m, 2H), 3.29 (s, 1H), 3.37 (s, 1H), 3.57 (s, 2H), 7.15 (d, $^3J_{H-H}$=9 Hz, 1H), 8.07 (d of d, $^3J_{H-H}$=9 Hz, $^4J_{H-H}$=2.7 Hz, 1H), 8.88 (d, $^4J_{H-H}$=2.7 Hz). $^{13}$C nmr (75.45 MHz, CDCl$_3$) δ (ppm): 28.15, 28.20, 29.48, 50.00 (br), 55.97, 56.28, 81.83, 82.68, 83.29, 118.27, 124.18, 127.44, 131.13, 141.95, 161.31, 172.67, 173.62.

TABLE 1

Crystal data for 1,4,7,10-Tetraazacyclododecane-1,4,7-triacetic acid, 10-[(2-t-butoxy-5-nitrophenyl)-methyl]-, tri-t-butyl ester, sodium bromide complex, Compound III.

| | |
|---|---|
| Identification code | m16205/lt/B3389P096 |
| Empirical formula | $C_{37}H_{65}BrN_5NaO_{10}$ |
| Formula weight | 842.84 |
| Temperature | 100 (2) K |
| Wavelength | 0.71073 Å |
| Crystal system | Monoclinic |
| Space group | $P2_1/c$ |
| Unit cell dimensions | a = 17.4523 (8) Å  α = 99°. |
| | b = 22.6145 (9) Å  β = 92.550 (3)°. |
| | c = 10.9031 (5) Å  γ = 90°. |
| Volume | 4298.9 (3) Å$^3$ |
| Z | 4 |
| Density (calculated) | 1.302 Mg/m$^3$ |
| Absorption coefficient | 1.024 mm$^{-1}$ |
| F(000) | 1792 |
| Crystal size | 0.30 × 0.19 × 0.13 mm$^3$ |
| Theta range for data collection | 1.47 to 26.43°. |
| Index ranges | $-21 \leq h \leq 21, -28 \leq k \leq 28,$ |
| | $-13 \leq l \leq 13$ |
| Reflections collected | 116780 |
| Independent reflections | 8831 [R(int) = 0.112] |
| Completeness to theta = 26.43° | 99.8% |
| Absorption correction | Semi-empirical from equivalents |
| Max. and min. transmission | 0.8784 and 0.7487 |
| Refinement method | Full-matrix least-squares on F$^2$ |
| Data/restraints/parameters | 8831/0/495 |
| Goodness-of-fit on F$^2$ | 1.021 |
| Final R indices [I > 2sigma(I)] | R1 = 0.0424, wR2 = 0.0744 |
| R indices (all data) | R1 = 0.0787, wR2 = 0.0867 |
| Largest diff. peak and hole | 0.385 and −0.340 e · Å$^{-3}$ |

Figure 3:
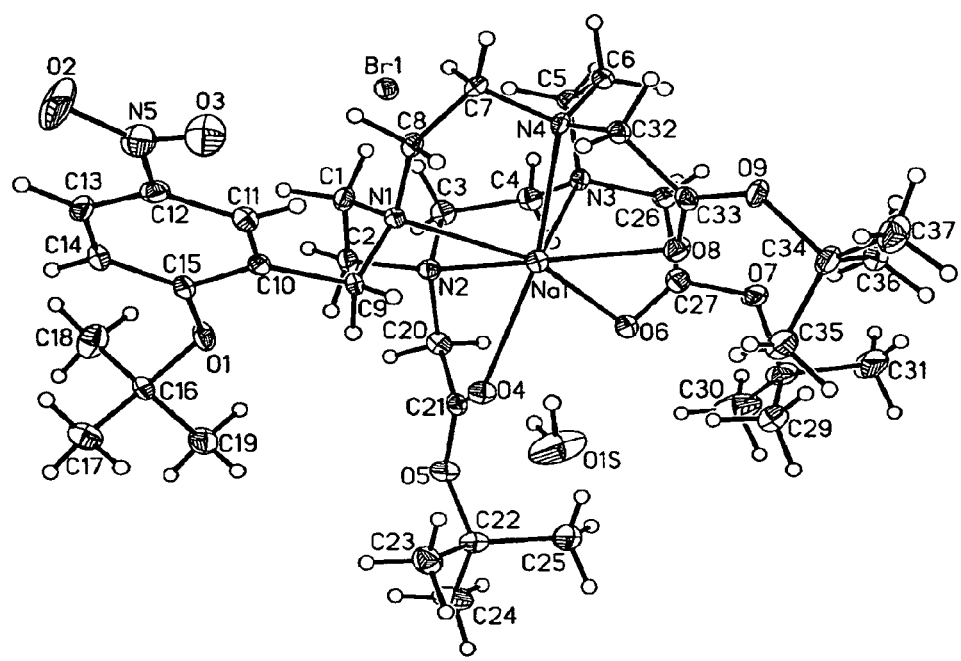
FIG. 3 is an illustration of a projection view of 1,4,7,10-Tetraazacyclododecane-1,4,7-triacetic acid, 10-[(2-t-butoxy-5-nitrophenyl)-methyl]-, tri-t-butyl ester, sodium bromide complex, Compound III, with 50% thermal ellipsoids.

A projection view of the molecule with 50% thermal ellipsoids is illustrated in FIG. 3.

Figure 4:
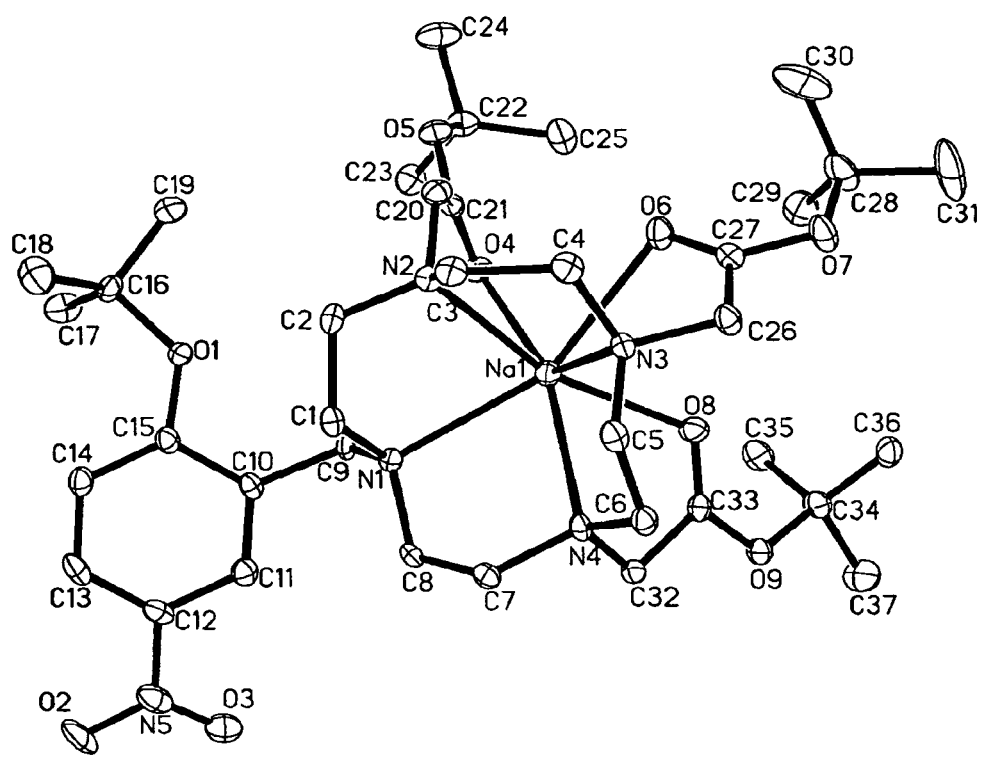
FIG. 4 is an illustration of a projection view of 1,4,7,10-Tetraazacyclododecane-1,4,7-triacetic acid, 10-[(2-t-butoxy-5-nitrophenyl)-methyl]-, tri-t-butyl ester, sodium bromide complex, Compound III, with 50% thermal ellipsoids, wherein anion, solvent water and H atoms not shown for clarity.

A projection view of the molecule with 50% thermal ellipsoids is illustrated in FIG. 4. Anion, solvent water and H atoms not shown for clarity.

EXAMPLE 2

Figure 5:
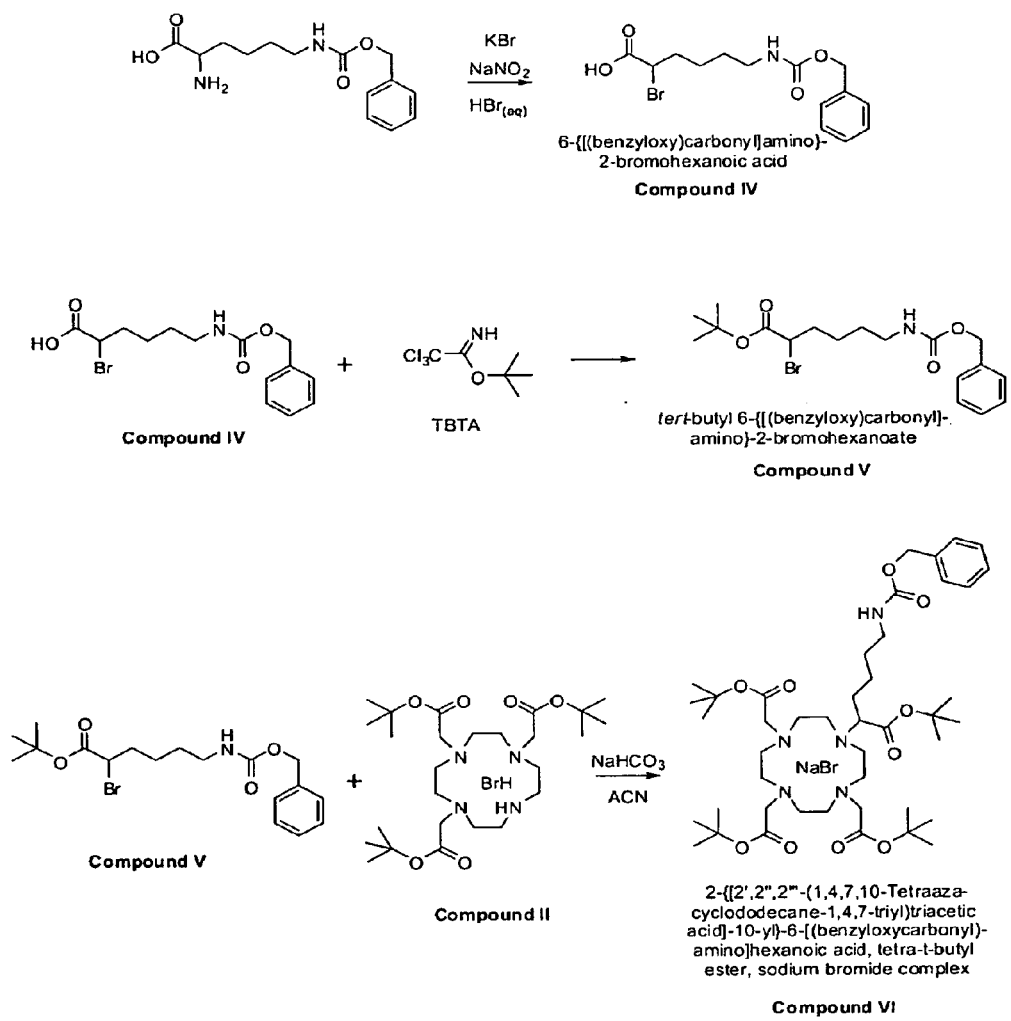
FIG. 5 is an illustration of a reaction synthesis of (S)-6-{[(Benzyloxy)carbonyl]amino}-2-bromohexanoic acid, Compound IV, tert-Butyl 6-{[(benzyloxy)carbonyl]amino}-2-bromohexanoate, Compound V, and 2-{[2',2",2'''-(1,4,7,10-Tetraazacyclododecane-1,4,7-triyl)tri acetic acid]-10-yl}-6-[(benzyl-oxycarbonyl)amino]hexanoic acid, tetra-t-butyl ester, sodium bromide complex, Compound VI.

Synthesis of 2-{[2',2'',2'''-(1,4,7,10-Tetraazacyclododecane-1,4,7-triyl)triacetic acid]-10-yl}-6-[(benzyloxycarbonyl)amino]hexanoic acid, tetra-t-butyl ester, sodium bromide complex, Compound VI The synthesis of (S)-6-{[(Benzyloxy)carbonyl]amino}-2-bromohexanoic acid, Compound IV, tert-Butyl 6-{[(benzyloxy)carbonyl]amino}-2-bromohexanoate, Compound V, and 2-{[2',2'',2'''-(1,4,7,10-Tetraazacyclododecane-1,4,7-triyl)triacetic acid]-10-yl}6-[(benzyl-oxycarbonyl)amino]hexanoic acid, tetra-t-butyl ester, sodium bromide complex, Compound VI, are illustrated in FIG. 5.

(S)-6-{[(Benzyloxy)carbonyl]amino}-2-bromohexanoic acid, Compound IV. (S-2-Amino-6-{[(benzyloxy)carbonyl]amino}hexanoic acid, 20.0 g (0.14 mole), and potassium bromide, 28.9 g (0.24 mole), were dissolved in 80 mL of ~6N aqueous HBr, previously chilled to 0° C. A stream of nitrogen was bubbled through the solution and the mixture was chilled to −10° C. by means of a cold bath. Sodium nitrite, 5.9 g (0.86 mole) was added in portions over 30 min with stirring, while maintaining the temperature of the reaction from −13° C. to −10° C. After 6 hours stirring at −10° C., the mixture was extracted with ethyl ether, 4×50 mL and the resulting solution dried with magnesium sulfate. The mixture was filtered to remove the drying agent and evaporated to give an orange oil. The oil was purified by flash chromatography, chloroform-hexanes to give a clear and colorless oil. The yield was 20.0 g, i.e., 81%, based on starting 2-amino-6-{[(benzyl-oxy)carbonyl]-amino}hexanoic acid. NMR is consistent with structure. (Nicolaides et al.)

tert-Butyl 6-{[(benzyloxy)carbonyl]amino}-2-bromohexanoate, Compound V. (S)-6-{[(Benzyl-oxy)carbonyl]amino}-2-bromohexanoic acid, 10.0 g (0.029 mole), was dissolved in chloroform, 20 mL. To this was added a solution of t-butyl trichloroacetimidate, 12.7 g (0.058 mole), dissolved in chloroform, 50 mL, drop-wise over 30 minutes. The mixture was allowed to stir an additional 5 minutes and boron trifluoride etherate, 100 µL, was added. The reaction mixture was allowed to stir overnight. Sodium bicarbonate, 5 g, was added. After stirring 10 minutes, hexanes, 50 mL, was added and the mixture filtered to remove the solids present. The filtrate was evaporated and the residue purified by flash chromatography, ethyl acetate-hexanes, to give a clear-colorless oil. The yield was 8.5 g, 73% based on starting (S)-6-{[(benzyloxy)carbonyl]amino}-2-bromohexanoic acid. NMR is consistent with structure.

2-{[2',2'',2'''-(1,4,7,10-Tetraazacyclododecane-1,4,7-triyl)triacetic acid]-10-yl}-6-[(benzyl-oxycarbonyl)amino]hexanoic acid, tetra-t-butyl ester, sodium bromide complex, Compound VI. 1,4,7,10-Tetraazacyclododecane-1,4,7-triacetic acid, tri-t-butyl ester hydrobromide, 5.95 g (0.0100 mole), was stirred with aqueous sodium hydroxide, 0.1N 110 mL, and diethyl ether, 150 mL. When the entire solid had dissolved, the organic phase was collected and the aqueous phase washed with diethyl ether, 3×50 mL. The combined organic extracts were washed with 1×50 mL saturated aqueous sodium chloride, dried with magnesium sulfate, filtered and evaporated, under reduced pressure, to an oil. The oil was dissolved in acetonitrile, 50 mL. To this solution was added sodium bicarbonate, 0.84 g (0.0100 mole). The mixture was warmed to 30° C. A solution of tert-butyl 6-{[(benzyloxy)carbonyl]-amino}-2-bromohexanoate, 4.00 g (0.0100 mole), in acetonitrile, 50 mL, was added dropwise and the mixture was stirred overnight under argon. The resulting mixture was filtered and the filtrate concentrated under reduced pressure to give an amber foam. The foam was dissolved in diethyl ether, 100 mL, with stirring. The solution was concentrated to approximately 20 mL and stirred for one hour at room temperature. After the onset of crystallization, the mixture was cooled to −10° C. to complete crystallization. The product was collected by filtration, washed with cold, hexanes-ether (1:1) and vacuum dried. The yield was 3.60 g, 38% based on starting tert-butyl 6-{[(benzyloxy)carbonyl]-amino}-2-bromohexanoate. Anal. Calc. C, 55.34; H, 8.13; N, 7.33; Br, 8.37; Na, 2.41. Found C, 55.71; H, 8.22; N, 7.31; Br, 8.18; Na, 2.37. The NMR is consistent with the structure.

EXAMPLE 3

Figure 6:
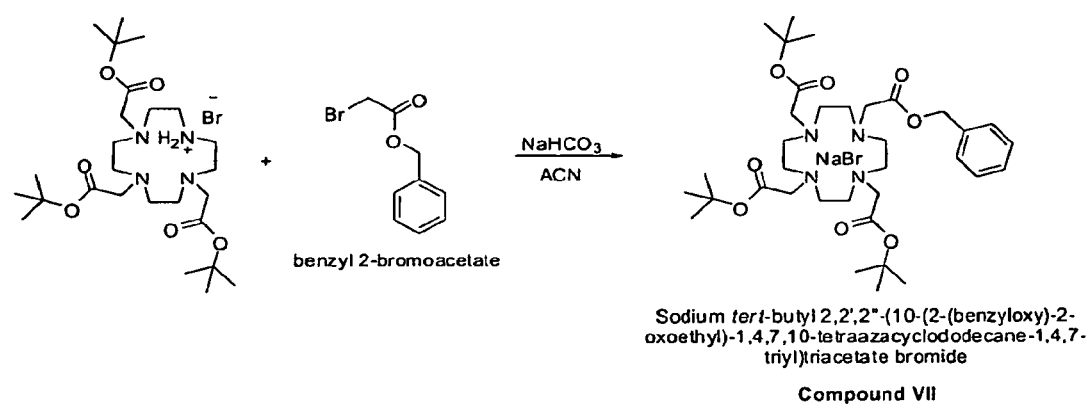
FIG. 6 is an illustration of a reaction synthesis of sodium tert-butyl 2,2',2"-(10-(2-(benzyloxy)-2-oxoethyl)-1,4,7,10-tetraazacyclododecane-1,4,7-triyl)triacetate bromide, Compound VII.

Synthesis of sodium tert-butyl 2,2',2''-(10-(2-(benzyloxy)-2-oxoethyl)-1,4,7,10-tetraazacyclododecane-1,4,7-triyl)triacetate bromide, Compound VII The synthesis of sodium tert-butyl 2,2',2''-(10-(2-(benzyloxy)-2-oxoethyl)-1,4,7,10-tetraazacyclododecane-1,4,7-triyl)triacetate bromide, Compound VII, is illustrated in FIG. 6.

Sodium tert-butyl 2,2',2''-(10-(2-(benzyloxy)-2-oxoethyl)-1,4,7,10-tetraazacyclododecane-1,4,7-triyl)triacetate bromide, Compound VII. 1,4,7,10-Tetraazacyclododecane-1,4,7-triacetic acid, tri-t-butyl ester hydrobromide, 10.0 g (0.0168 mole), was stirred with aqueous sodium hydroxide, 0.1N 150 mL, and diethyl ether, 150 mL. When the entire solid had dissolved, the organic phase was collected and the aqueous phase washed with diethyl ether, 3×50 mL. The combined organic extracts were washed with 1×50 mL saturated aqueous sodium chloride, dried with magnesium sulfate, filtered and evaporated, under reduced pressure, to an oil, 7.9 g (0.0153 mole as the free base). The oil was dissolved in acetonitrile, 100 mL. To this solution was added sodium bicarbonate, 1.29 g (0.0153 mole). The mixture was warmed to 30° C. A solution of benzyl 2-bromoacetate, 3.52 g (0.0153 mole), in acetonitrile, 100 mL, was added dropwise and the mixture was stirred overnight under argon. The resulting mixture was filtered and the filtrate concentrated under reduced pressure to give a clear colorless oil. The oil was dissolved in diethyl ether, 100 mL, with stirring. The product began crystallizing after a few minutes. After stirring for ca. 1 hr, the product was collected by filtration, washed with fresh ether and vacuum dried. The yield was 9.7 g, 83% based on starting benzyl 2-bromoacetate. Anal. Calc. % C, 54.90; H, 7.63; N, 7.32; Na, 3.00; Br, 10.43. Found C, 54.96; H, 7.67; N, 7.33; Na, 2.85; Br, 10.24. The NMR is consistent with the structure.

EXAMPLE 4

Figure 7:
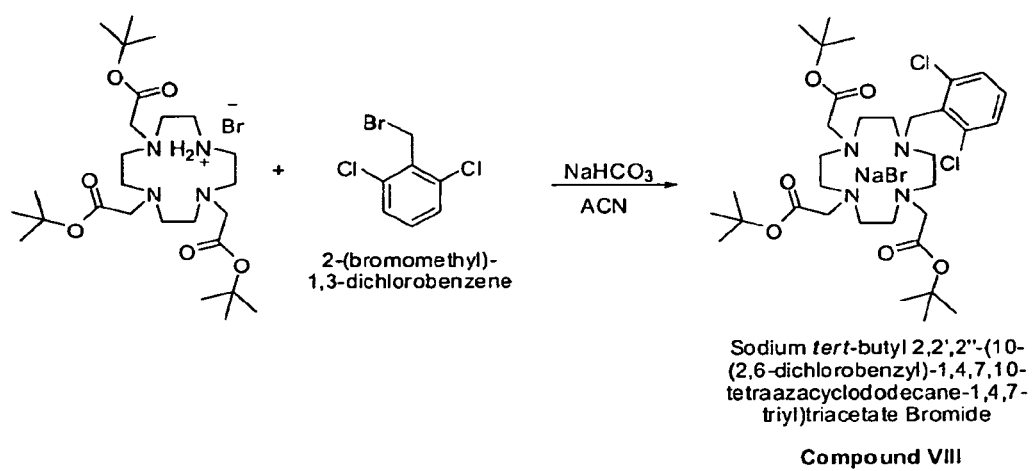
FIG. 7 is an illustration of a reaction synthesis of sodium tert-butyl 2,2',2"-(10-(2,6-dichlorobenzyl)-1,4,7,10-tetraazacyclododecane-1,4,7-triyl)triacetate Bromide, Compound VIII.

Synthesis of sodium tert-butyl 2,2',2''-(10-(2,6-dichlorobenzyl)-1,4,7,10-tetraazacyclododecane-1,4,7-triyl)triacetate Bromide, Compound VIII The synthesis of sodium tert-butyl 2,2',2''-(10-(2,6-dichlorobenzyl)-1,4,7,10-tetraazacyclododecane-1,4,7-triyl)triacetate Bromide, Compound VIII, is illustrated in FIG. 7.

Synthesis of sodium tert-butyl 2,2',2''-(10-(2,6-dichlorobenzyl)-1,4,7,10-tetraazacyclododecane-1,4,7-triyl)triacetate Bromide, Compound VIII. 1,4,7,10-Tetraazacyclododecane-1,4,7-triacetic acid, tri-t-butyl ester hydrobromide, 10.0 g (0.0168 mole), was stirred with aqueous sodium hydroxide, 0.1N 150 mL, and diethyl ether, 150 mL. When the entire solid had dissolved, the organic phase was collected and the aqueous phase washed with diethyl ether, 3×50 mL. The combined organic extracts were washed with 1×50 mL saturated aqueous sodium chloride, dried with magnesium sulfate, filtered and evaporated, under reduced pressure, to an oil, 8.6 g (0.0167 mole as the free base). The oil was dissolved in acetonitrile, 100 mL. To this solution was added sodium bicarbonate, 1.40 g (0.0167 mole). The mixture was warmed to 30° C. A solution of 2-bromomethyl-1,3-dichlorobenzene, 4.01 g (0.0167 mole), in acetonitrile, 100 mL, was added dropwise and the mixture was stirred overnight under argon. The resulting mixture was filtered and the filtrate concentrated under reduced pressure to give a clear colorless oil. The oil was dissolved in diethyl ether, 100 mL, with stirring. The product began crystallizing after a few minutes. After stirring for ca. 1 hr, the product was collected by filtration, washed with fresh ether and vacuum dried. The yield was 10.0 g, 77% based on starting 2-bromomethyl-1,3-dichlorobenzene. Anal. Calc. % C, 51.04; H, 7.01; N, 7.21; Na, 2.96; Br, 10.29. Found C, 50.11; H, 7.38; N, 6.95; Na, 2.92; Br, 10.72. The NMR is consistent with the structure. Single crystals suitable for X-ray analysis were grown from chloroform-hexanes.

TABLE 2

Crystal data for sodium tert-butyl 2,2',2''-(10-(2,6-dichlorobenzyl)-1,4,7,10-tetraazacyclododecane-1,4,7-triyl)triacetate Bromide, VIII.

| | |
|---|---|
| Identification code | t8106lt/B3401P061 |
| Empirical formula | $C_{36}H_{57}BrCl_{11}N_4NaO_6$ |
| Formula weight | 1134.71 |
| Temperature | 100 (2) K |

TABLE 2-continued

Crystal data for sodium tert-butyl 2,2',2''-(10-(2,6-dichlorobenzyl)-1,4,7,10-tetraazacyclododecane-1,4,7-triyl)triacetate Bromide, VIII.

| | |
|---|---|
| Wavelength | 0.71073 Å |
| Crystal system | Triclinic |
| Space group | P-1 |
| Unit cell dimensions | a = 11.2161 (8) Å   α = 104.591 (5)°. |
| | b = 21.0334 (15) Å   β = 97.041 (5)°. |
| | c = 24.3047 (18) Å   γ = 103.280 (4)°. |
| Volume | 5300.4 (7) Å$^3$ |
| Z | 4 |
| Density (calculated) | 1.422 Mg/m$^3$ |
| Absorption coefficient | 1.381 mm$^{-1}$ |
| F(000) | 2328 |
| Crystal size | 0.28 × 0.22 × 0.12 mm$^3$ |
| Theta range for data collection | 1.15 to 25.01°. |
| Index ranges | $-13 \leq h \leq 13, -25 \leq k \leq 25,$ |
| | $-28 \leq l \leq 28$ |
| Reflections collected | 132441 |
| Independent reflections | 18599 [R(int) = 0.13] |
| Completeness to theta = 25.01° | 99.6% |
| Absorption correction | Numerical |
| Max. and min. transmission | 0.8909 and 0.7761 |
| Refinement method | Full-matrix least-squares on F$^2$ |
| Data/restraints/parameters | 18599/0/1102 |
| Goodness-of-fit on F$^2$ | 1.235 |
| Final R indices [I > 2sigma(I)] | R1 = 0.0822, wR2 = 0.2054 |
| R indices (all data) | R1 = 0.1462, wR2 = 0.2375 |
| Largest diff. peak and hole | 1.627 and −1.032 e · Å$^{-3}$ |

Figure 8:
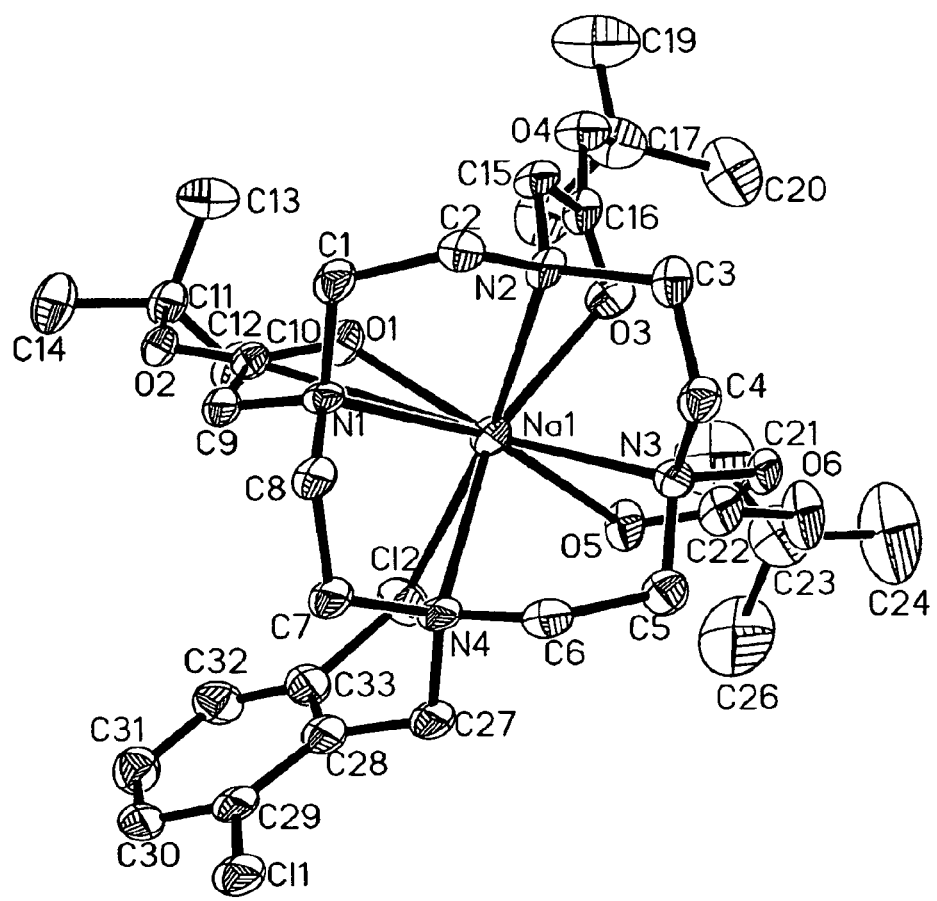
FIG. 8 is a projection view of sodium tert-butyl 2,2',2"-(10-(2,6-dichlorobenzyl)-1,4,7,10-tetraazacyclododecane-1,4,7-triyl)triacetate bromide, Compound VIII, with 50% thermal ellipsoids, wherein one unique molecule shown. Solvents, counter ions and H atoms are not shown for clarity.

FIG. 8 provides a projection view of sodium tert-butyl 2,2',2''-(10-(2,6-dichlorobenzyl)-1,4,7,10-tetraazacyclododecane-1,4,7-triyl)triacetate bromide, Compound VIII, with 50% thermal ellipsoids, wherein one unique molecule shown. Solvents, counter ions and H atoms are not shown for clarity.

Figure 9:
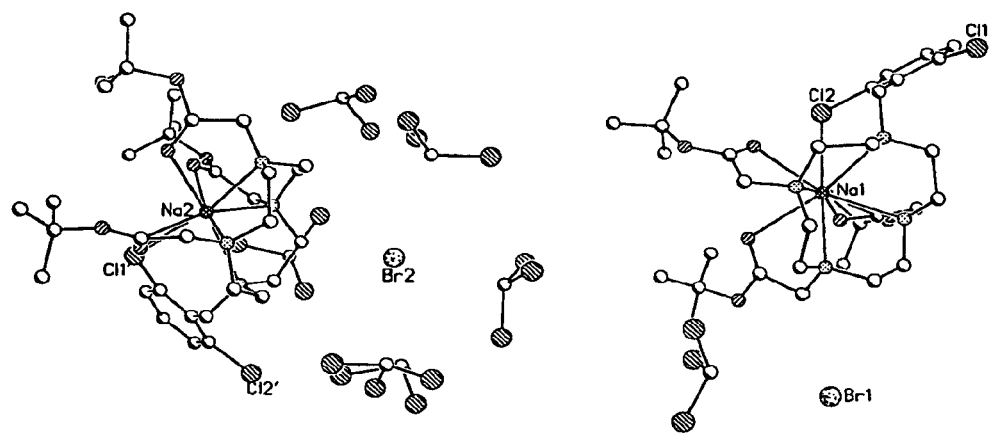
FIG. 9 is a projection view of sodium tert-butyl 2,2',2"-(10-(2,6-dichlorobenzyl)-1,4,7,10-tetraazacyclododecane-1,4,7-triyl)triacetate Bromide, Compound VIII.

FIG. 9 provides a projection view of sodium tert-butyl 2,2',2''-(10-(2,6-dichlorobenzyl)-1,4,7,10-tetraazacyclododecane-1,4,7-triyl)triacetate Bromide, Compound VIII.

EXAMPLE 5

Figure 10:
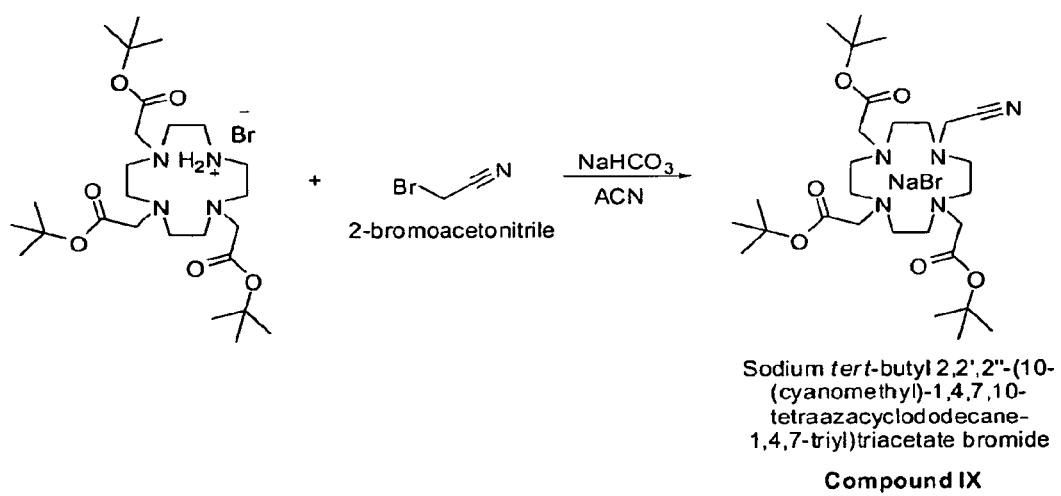
FIG. 10 is an illustration of a reaction synthesis of sodium tert-butyl 2,2',2"-(10-(cyanomethyl)-1,4,7,10-tetraazacyclododecane-1,4,7-triyl)triacetate bromide, Compound IX.

Synthesis of sodium tert-butyl 2,2',2''-(10-(cyanomethyl)-1,4,7,10-tetraazacyclododecane-1,4,7-triyl) triacetate bromide, Compound IX FIG. 10 provides an illustration of a reaction synthesis of sodium tert-butyl 2,2',2''-(10-(cyanomethyl)-1,4,7,10-tetraazacyclododecane-1,4,7-triyl)triacetate bromide, Compound IX.

1,4,7,10-Tetraazacyclododecane-1,4,7-triacetic acid, tri-t-butyl ester hydrobromide, 25.0 g (0.0420 mole), was stirred with aqueous sodium hydroxide, 0.1N 600 mL, and diethyl ether, 200 mL. When the entire solid had dissolved, the organic phase was collected and the aqueous phase washed with diethyl ether, 3×100 mL. The combined organic extracts were washed with 1×50 mL saturated aqueous sodium chloride, dried with magnesium sulfate, filtered and evaporated, under reduced pressure, to an oil, 19.1 g (0.0371 mole as the free base). The oil was dissolved in acetonitrile, 250 mL. To this solution was added sodium bicarbonate, 3.12 g (0.0371 mole). The mixture was warmed to 30° C. A solution of 2-bromoacetonitrile, 4.45 g (0.0371 mole), in acetonitrile, 100 mL, was added dropwise and the mixture was stirred overnight under argon. The resulting mixture was filtered and the filtrate concentrated under reduced pressure to give a clear colorless oil. The oil was dissolved in diethyl ether, 200 mL, with stirring. The product began crystallizing after a few minutes. After stirring for ca. 1 hr, the product was collected by filtration, washed with fresh ether and vacuum dried. The yield was 20.0 g, 82% based on starting bromoacetonitrile. Anal. Calc. % C, 51.22; H, 7.83; N, 10.67; Na, 3.50; Br, 12.17. Found C, 51.06; H, 7.88; N, 10.49; Na, 3.34; Br, 12.72. The NMR is consistent with the structure.

EXAMPLE 6

Figure 11:
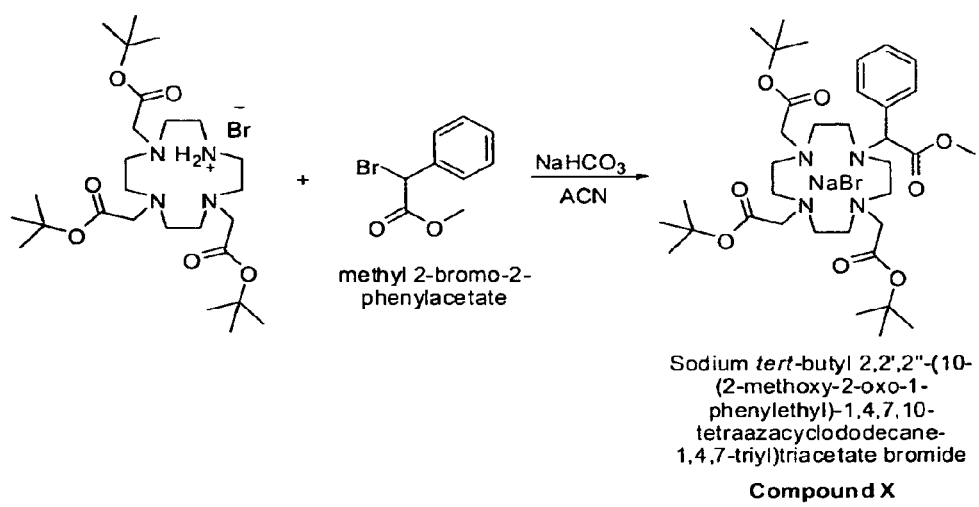
FIG. 11 is an illustration of a reaction synthesis of sodium tert-butyl 2,2',2"-(10-(2-methoxy-2-oxo-1-phenylethyl)-1,4,7,10-tetraazacyclododecane-1,4,7-triyl)triacetate bromide, Compound X.

Synthesis of sodium tert-butyl 2,2',2"-(10-(2-methoxy-2-oxo-1-phenylethyl)-1,4,7,10-tetraazacyclododecane-1,4,7-triyl)triacetate bromide, Compound X FIG. 11 provides an illustration of a reaction synthesis of sodium tert-butyl 2,2',2"-(10-(2-methoxy-2-oxo-1-phenylethyl)-1,4,7,10-tetraazacyclododecane-1,4,7-triyl)triacetate bromide, Compound X.

1,4,7,10-Tetraazacyclododecane-1,4,7-triacetic acid, tri-t-butyl ester hydrobromide, 5.5 g (0.0092 mole), was stirred with aqueous sodium hydroxide, 0.1N 100 mL, and diethyl ether, 100 mL. When the entire solid had dissolved, the organic phase was collected and the aqueous phase washed with diethyl ether, 3×25 mL. The combined organic extracts were washed with 1×25 mL saturated aqueous sodium chloride, dried with magnesium sulfate, filtered and evaporated, under reduced pressure, to an oil, 2.20 g (0.0043 mole as the free base). The oil was dissolved in acetonitrile, 55 mL. To this solution was added sodium bicarbonate, 0.36 g (0.0043 mole). The mixture was warmed to 30° C. A solution of methyl 2-bromo-2-phenylacetate, 0.98 g (0.0043 mole), in acetonitrile, 10 mL, was added dropwise and the mixture was stirred overnight under argon. The resulting mixture was filtered and the filtrate concentrated under reduced pressure to give a clear colorless oil. The oil was dissolved in diethyl ether, 50 mL, with stirring. The product began crystallizing after a few minutes. After stirring for ca. 1 hr, the product was collected by filtration, washed with fresh ether and vacuum dried. The yield was 3.3 g, 100% based on starting methyl 2-bromo-2-phenylacetate. Anal. Calc. %. C, 54.90; H, 7.63; N, 7.32; Na, 3.00; Br, 10.43. Found C, 54.61; H, 7.69; N, 7.10; Na, 2.78; Br, 10.57. The NMR is consistent with the structure. Single crystals suitable for X-ray analysis were grown from chloroform-hexanes.

TABLE 3

Crystal data for sodium tert-butyl 2,2',2"-(10-(2-methoxy-2-oxo-1-phenylethyl)-1,4,7,10-tetraazacyclodo-decane-1,4,7-triyl)triacetate bromide, Compound X.

| | |
|---|---|
| Identification code | t8406/lt/B3401P064 |
| Empirical formula | $C_{39}H_{62}BrCl_{12}N_4NaO_8$ |
| Formula weight | 1243.23 |
| Temperature | 100 (2) K |
| Wavelength | 0.71073 Å |
| Crystal system | Orthorhombic |
| Space group | Pbca |
| Unit cell dimensions | a = 13.9131 (5) Å   α = 90°. |
| | b = 21.8801 (8) Å   β = 90°. |
| | c = 37.7462 (14) Å  β = 90°. |
| Volume | 11490.7 (7) Å$^3$ |
| Z | 8 |
| Density (calculated) | 1.437 Mg/m$^3$ |
| Absorption coefficient | 1.328 mm$^{-1}$ |
| F(000) | 5104 |
| Crystal size | 0.37 × 0.12 × 0.09 mm$^3$ |
| Theta range for data collection | 1.82 to 25.01°. |
| Index ranges | −16 <= h <= 16, −26 <= k <= 26, −44 <= l <= 44 |
| Reflections collected | 0220036 |
| Independent reflections | 10119 [R(int) = 0.23] |
| Completeness to theta = 25.01° | 99.9% |
| Absorption correction | Semi-empirical from equivalents |
| Max. and min. transmission | 0.8898 and 0.6393 |
| Refinement method | Full-matrix least-squares on F$^2$ |
| Data/restraints/parameters | 10119/2/624 |
| Goodness-of-fit on F$^2$ | 1.211 |
| Final R indices [I > 2sigma(I)] | R1 = 0.0688, wR2 = 0.1244 |
| R indices (all data) | R1 = 0.1381, wR2 = 0.1443 |
| Largest diff. peak and hole | 0.590 and −0.574 e · Å$^{-3}$ |

Figure 12:
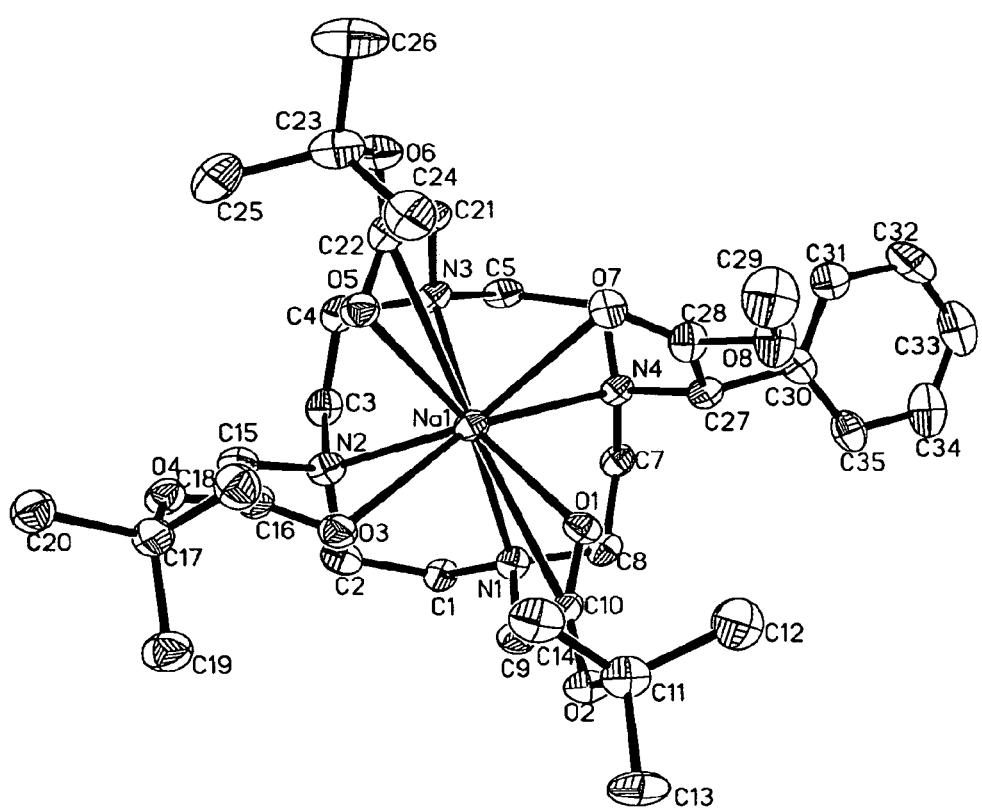
FIG. 12 is a projection view of sodium tert-butyl 2,2',2"-(10-(2-methoxy-2-oxo-1-phenylethyl)-1,4,7,10-tetraazacyclododecane-1,4,7-triyl)triacetate bromide, Compound X, with 50% thermal ellipsoids. Solvents, counter ions and H atoms are not shown for clarity.

Projection view of sodium tert-butyl 2,2',2"-(10-(2-methoxy-2-oxo-1-phenylethyl)-1,4,7,10-tetraazacyclodo-decane-1,4,7-triyl)triacetate bromide, Compound X, with 50% thermal ellipsoids is illustrated in FIG. 12. The counter ion, H atoms and solvents not shown for clarity.

Figure 13:
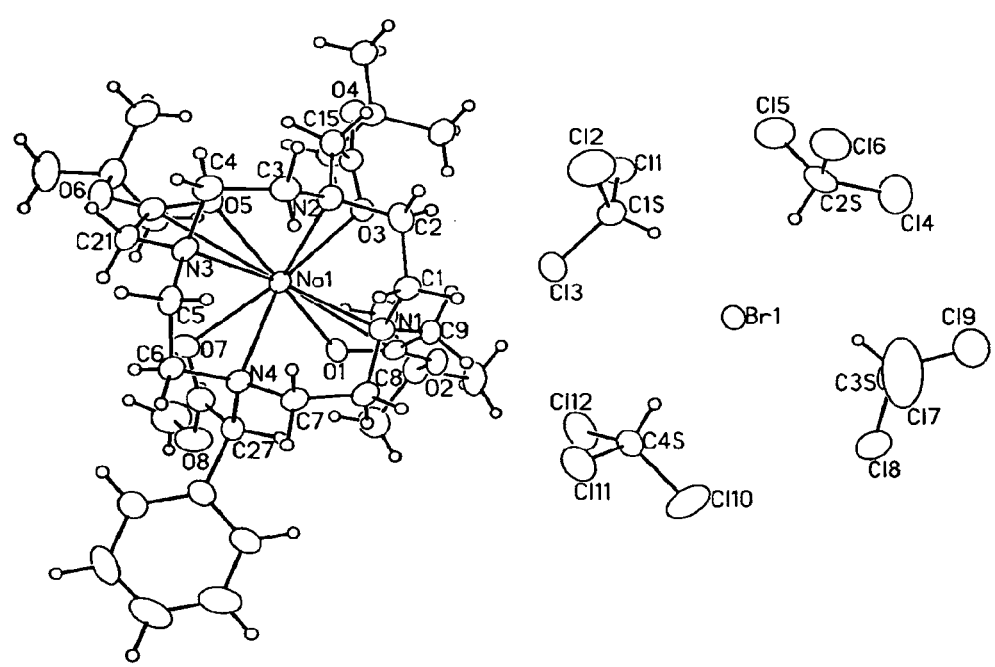
FIG. 13 is a projection view of sodium tert-butyl 2,2',2"-(10-(2-methoxy-2-oxo-1-phenylethyl)-1,4,7,10-tetraazacyclodo-decane-1,4,7-triyl)triacetate bromide, Compound X, with 50% thermal ellipsoids, wherein disorder Cl atoms are not shown.

FIG. 13 is a projection view of sodium tert-butyl 2,2',2"-(10-(2-methoxy-2-oxo-1-phenylethyl)-1,4,7,10-tetraazacyclodo-decane-1,4,7-triyl)triacetate bromide, Compound X, with 50% thermal ellipsoids, wherein disorder Cl atoms are not shown.

EXAMPLE 7

Figure 14:
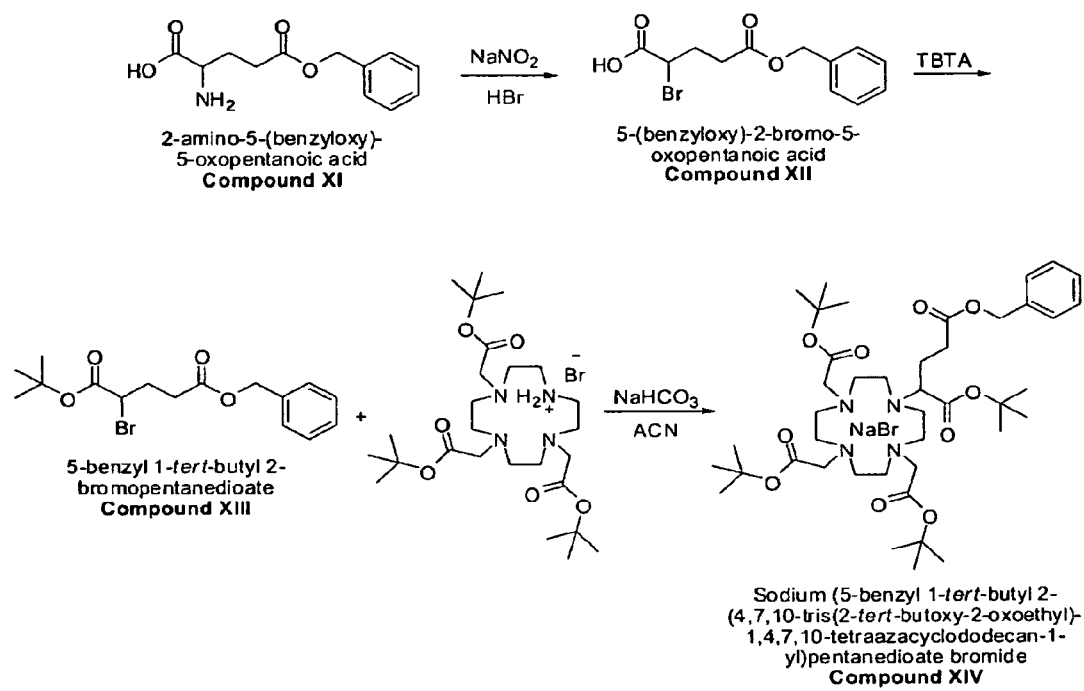
FIG. 14 is an illustration of a reaction synthesis of 2-amino-5-(benzyloxy)-5-oxopentanoic acid, Compound XI; 5-(benzyloxy)-2-bromo-5-oxopentanoic acid, Compound XII; 5-benzyl 1-tert-butyl 2-bromopentanedioate, Compound XIII; and Sodium (5-benzyl 1-tert-butyl 2-(4,7,10-tris(2-tert-butoxy-2-oxoethyl)-1,4,7,10-tetraazacyclododecan-1-yl) pentanedioate bromide, Compound XIV.

Synthesis of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV FIG. 14 provides illustration of a reaction synthesis of 2-amino-5-(benzyloxy)-5-oxopentanoic acid, Compound XI; 5-(benzyloxy)-2-bromo-5-oxopentanoic acid, Compound XII; 5-benzyl 1-tert-butyl 2-bromopentanedioate, Compound XIII; and sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV.

5-(Benzyloxy)-2-bromo-5-oxopentanoic acid, XII. 2-Amino-5-(benzyloxy)-5-oxopentanoic acid, 20.00 g (0.084 mole), and potassium bromide, 34.1 g (0.29 mole), were dissolved in 80 mL of ~6N aqueous HBr, previously chilled to 0° C. A stream of nitrogen was bubbled through the solution and the mixture was chilled to −10° C. by means of a cold bath. Sodium nitrite, 6.98 g (0.10 mole) was added in portions over 30 min with stirring, while maintaining the temperature of the reaction from −13° C. to −10° C. After 6 hours stirring at −10° C., the mixture was extracted with ethyl ether, 4×100 mL and the resulting solution dried with magnesium sulfate. The mixture was filtered to remove the drying agent and evaporated to give an orange oil. The oil was purified by flash chromatography, chloroform-hexanes to give a clear and colorless oil. The yield was 11.5 g, i.e., 45%, based on starting 2-amino-{[(benzyl-oxy)-5-oxopentanoic acid. NMR is consistent with structure.

5-(Benzyl) 1-tert-butyl 2-brompentandioate, Compound XIII. 5-(Benzyloxy)-2-bromo-5-oxopentanoic acid, 10.0 g (0.033 mole), was dissolved in chloroform, 20 mL. To this was added a solution of t-butyl trichloroacetimidate, 15.9 g (0.073 mole), dissolved in cyclohexane, 50 mL, drop-wise over 30 minutes. The mixture was allowed to stir an additional 5 minutes and boron trifluoride etherate, 100 μL, was added. The reaction mixture was allowed to stir overnight. Sodium bicarbonate, 5 g, was added. After stirring 10 minutes, hexanes, 50 mL, was added and the mixture filtered to remove the solids present. The filtrate was evaporated and the residue purified by flash chromatography, ethyl acetate-hexanes, to give a clear-colorless oil. The yield was 8.2 g, 69% based on starting 5-(Benzyloxy)-2-bromo-5-oxopentanoic acid. NMR is consistent with structure.

Synthesis of Sodium (5-benzyl 1-tert-butyl 2-(4,7,10-tris (2-tert- butoxy-2-oxoethyl)-1,4,7,10-tetraazacyclododecan-1-yl)pentanedioate bromide, Compound XIV. 1,4,7,10-Tetraazacyclododecane-1,4,7-triacetic acid, tri-t-butyl ester hydrobromide, 10.0 g (0.0168 mole), was stirred with aqueous sodium hydroxide, 0.1N 150 mL, and diethyl ether, 150 mL. When the entire solid had dissolved, the organic phase was collected and the aqueous phase washed with diethyl ether, 3×50 mL. The combined organic extracts were washed with 1×50 mL saturated aqueous sodium chloride, dried with magnesium sulfate, filtered and evaporated, under reduced pressure, to an oil, 8.8g (0.0171 mole as the free base). The oil was dissolved in acetonitrile, 100 mL. To this solution was added sodium bicarbonate, 1.51 g (0.0180 mole). The mixture was warmed to 30° C. A solution of 5-benzyl, 1-tert-butyl 2-bromopentandioate, 8.02 g (0.0180 mole), in acetonitrile, 40 mL, was added dropwise and the mixture was stirred overnight under argon. The resulting mixture was filtered and the filtrate concentrated under reduced pressure to give a clear colorless oil. The oil was dissolved in diethyl ether, 100 mL, with stirring. The product began crystallizing after a few minutes. After stirring for ca. 1 hr, the product was collected by filtration, washed with fresh ether and vacuum dried. NMR analysis revealed the solid, 9.3g, consisted of a mixture of Na-DO3A-tris (tert-butyl ester) bromide and the desired product. The solid was recrystallized twice from minimal ethyl acetate, ca.,100 mL ea., giving very pure product. The yield was 2.7 g, 18% based on starting 5-benzyl, 1-tern-butyl 2-bromopentandioate. Anal. Calc. As the monohydrate % C, 55.25; H, 7.44; N, 6.08; Br, 9.08; Na, 3.68. Found C, 55.32; H, 7.96; N, 6.14; Br, 8.76; Na. 2.52. The NMR is consistent with the structure. Crystal suitable for x-ray analysis were grown from ethyl acetate.

TABLE X

Crystal structure of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV.

| | |
|---|---|
| Identification code | m12906/lt/B3401P094 |
| Empirical formula | C42H74BrN4NaO11.50 |
| Formula weight | 921.95 |
| Temperature | 100 (2) K |
| Wavelength | 0.71073 Å |
| Crystal system | Triclinic |
| Space group | P1 |
| Unit cell dimensions | a = 12.2485 (5) Å  α = 86.843°. |
| | b = 14.4009 (6) Å  β = 89.712°. |
| | c = 14.2175 (6) Å  β = 77.508°. |
| Volume | 2393.74 (17) Å$^3$ |
| Z | 2 |
| Density (calculated) | 1.279 Mg/m$^3$ |
| Absorption coefficient | 0.927 mm$^{-1}$ |
| F(000) | 984 |
| Crystal size | 0.30 × 0.18 × 0.16 mm$^3$ |
| Theta range for data collection | 1.43 to 25.00°. |
| Index ranges | −14 ≦ h ≦ 14, |
| | −16 ≦ k ≦ 16, −16 ≦ l ≦ 16 |
| Reflections collected | 47541 |
| Independent reflections | 16011 [R(int) = 0.068] |
| Completeness to theta = 25.00° | 99.4% |
| Absorption correction | Numerical |
| Max. and min. transmission | 0.913 and 0.846 |
| Refinement method | Full-matrix least-squares on F$^2$ |
| Data/restraints/parameters | 16011/3/1081 |
| Goodness-of-fit on F$^2$ | 1.038 |

TABLE X-continued

Crystal structure of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV.

| | |
|---|---|
| Final R indices [I > 2sigma(I)] | R1 = 0.0685, wR2 = 0.1394 |
| R indices (all data) | R1 = 0.1212, wR2 = 0.1640 |
| Absolute structure parameter | 0.003 (9) |
| Largest diff. peak and hole | 1.281 and −1.615 e · Å$^{-3}$ |

Figure 15:
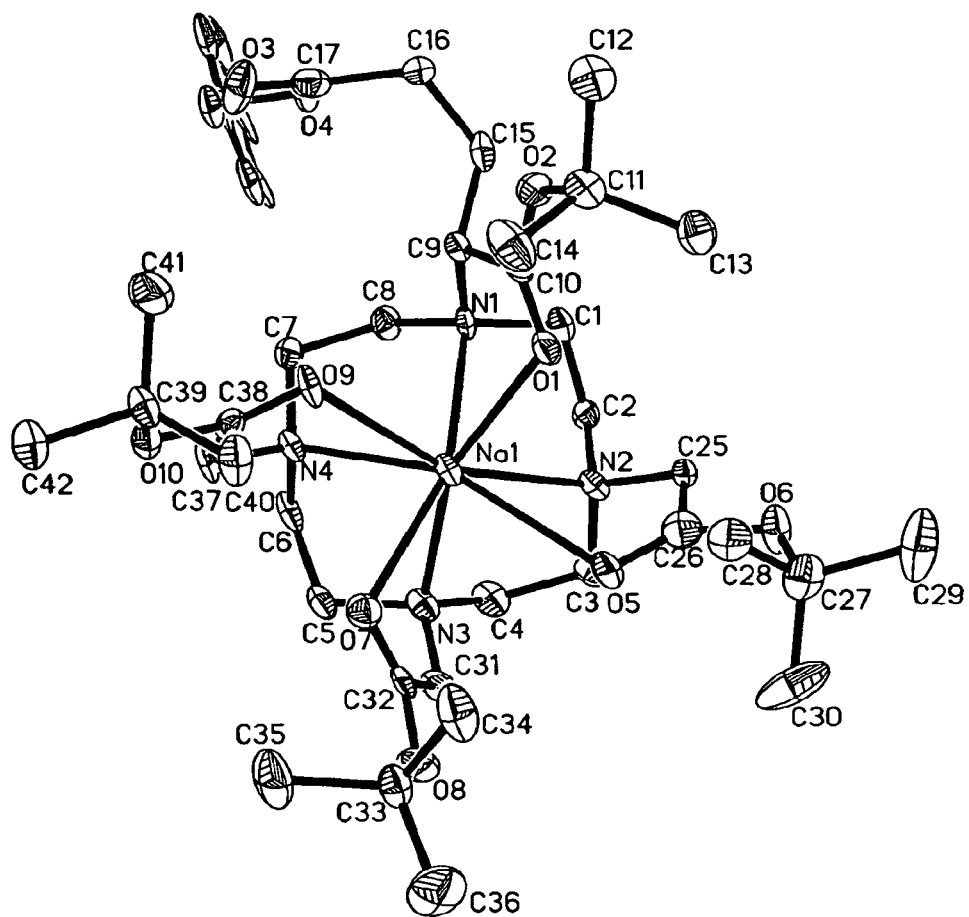
FIG. 15 is a projection view of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV, showing one of two molecules.

A projection view of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV, is illustrated in FIG. 15, wherein one of two molecules is shown and solvents, counter ions and H atoms are not shown for clarity.

Figure 16:
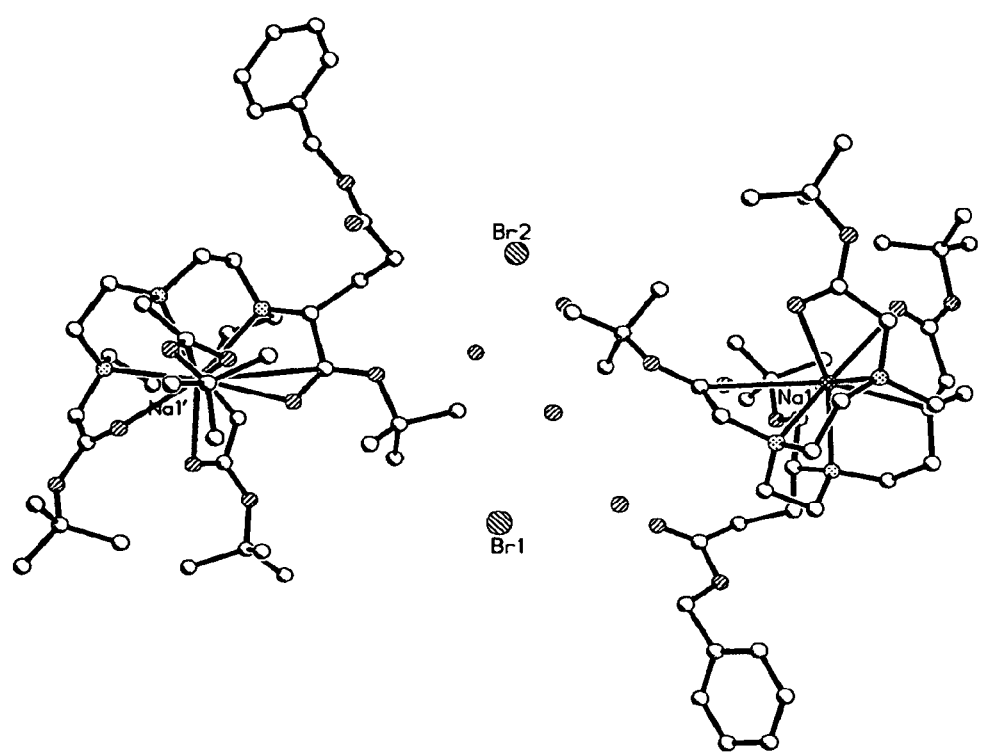
FIG. 16 is a projection view of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV.

A projection view of sodium (5-benzyl 1-tert-butyl 2-(4,7,10-tris(2-tert-butoxy-2-oxoethyl)-1,4,7,10-tetraazacyclododecan-1-yl)pentanedioate bromide, Compound XIV, is illustrated in FIG. 16.

REFERENCES

Armstrong, A., Brackenridge, I., Jackson, R. F. W., Kirk, J. M., "A New Method for the Preparation of Tertiary Butyl Ethers and Esters," Tetrahedron Lett. 1988, 29(20), 2483.

Himmelsbach, R. J., Rongved, P., Klavensess, J., Strande, P., Dugstad, H., "Hydroxamate and Hydrazide Derivatives of Polyamines and their Medical Use as Chelating Agents," PCT WO 93/02045, 1993.

Nicolaides, E. D.; Tinney, F. J.; Kaltenbronn, J. S.; Repine, J. T.; DeJohn, D. A; Lunney, E. A.; Roark, W. H., "Modified di- and tripeptides of the C-terminal portion of oxytocin and vasopressin as possible cognition activation agents," Journal of Medicinal Chemistry 1986, 29(6), 959-71.

The invention claimed is:

1. A process for alkylating the free macrocyclic nitrogen of a trisalkylated tetraazamacrocycle of Formula 1 to yield a compound of Formula 2, the process comprising alkylating the free macrocyclic nitrogen with an alkylating agent, R$_4$Y, in an organic solvent in the presence of a weak base

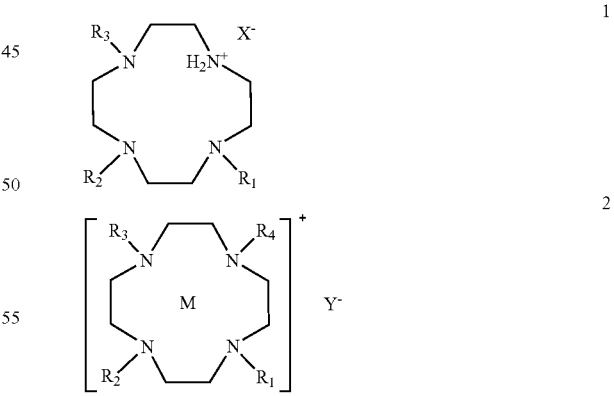

wherein the weak base comprises a metal ion M, R$_1$, R$_2$ and R$_3$ are independently hydrocarbyl, substituted hydrocarbyl or heterocyclo; R$_4$ is optionally substituted, alkyl or aryl, X is a counterion; and Y is a leaving group.

2. The process according to claim 1 wherein M is selected from alkali metals, alkaline earth metals, transition metals and the lanthanides; R$_1$, R$_2$ and R$_3$ are independently hydrocarbyl, substituted hydrocarbyl or heterocyclo; R$_4$ is an optionally substituted alkyl, aryl or acyl; X comprises halides, nitrates, sulfates or phosphates; and Y comprises the halides, methanesulfonate, trifluoroacetate, trifluormethanesulfonate or p-toluene-sulfonate.

3. The process according to claim 1 wherein $R_1$, $R_2$ and $R_3$ are independently selected from the group consisting of —$CH_2CO_2R_5$, —$CH_2ArOR_5$, —$CH_2SR_5$, —$CH_2PO_3H_2$, —$CH_2SO_3H$, —$CH_2Ar(OR_5)_2$, —$CH_2Ar(OR_5)R_6$ and —$CH_2Ar(OR_5)_2R_6$; wherein $R_5$ and $R_6$ are independently H, t-Bu, Et, Me, benzyl or methoxybenzyl.

4. The process according to claim 1 wherein $R_4$ is —$CH_2ArOR_7$, —$CH(R_8)CO_2R_7$, —$CH_2Ar(OR_7)_2$, —$CH_2Ar(OR_7)R_8$, or —$CH_2Ar(OR_7)_2R_8$; $R_7$ is H, t-Bu, Et or Me; $R_8$ is selected from the group consisting of optionally substituted acyl, aryl and heteroaryl, alkoxy, hydroxy, halo, amino, nitro, thiols, disulfides, carbohydrates, vitamins, and combinations and derivatives thereof; and Ar is an optionally substituted phenyl, pyrimidinyl or pyridinyl.

5. The process according to claim 1, wherein
$R_1$, $R_2$ and $R_3$ are independently selected from the group consisting of —$CH_2CO_2R_5$, —$CH_2ArOR_5$, —$CH_2SR_5$, —$CH_2PO_3H_2$, —$CH_2SO_3H$, —$CH_2Ar(OR_5)_2$, —$CH_2Ar(OR_5)R_6$ and —$CH_2Ar(OR_5)_2R_6$;

$R_4$ is —$CH_2ArOR_7$, —$CH(R_8)CO_2R_7$, —$CH_2Ar(OR_7)_2$, —$CH_2Ar(OR_7)R_8$, or —$CH_2Ar(OR_7)_2R_8$;

$R_5$, $R_6$ and $R_7$ are independently hydrogen, alkyl or substituted alkyl;

$R_8$ is selected from a group consisting of optionally substituted acyl, aryl and heteroaryl, alkoxy, hydroxy, halo, amino, nitro, thiols, disulfides, carbohydrates, vitamins, combinations and derivatives;

Ar is an optionally substituted phenyl, pyrimidinyl or pyridinyl; and

Y is a leaving group selected from the group consisting of bromide, chloride, iodide, methanesulfonate, trifluoroacetate, trifluormethanesulfonate and p-toluene-sulfonate.

6. The process according to claim 5 wherein $R_1$, $R_2$ and $R_3$ are independently —$CH_2CO_2R_5$; and $R_5$ is H, t-Bu, Et, Me, benzyl or benzylmethoxy.

7. The process according to claim 5 wherein $R_4$ is —$CH_2Ar(OR_5)NO_2$ or —$CH(CO_2R_5)$—$(CH_2)_4NHCO_2CH_2Ar$.

8. The process according to claim 7 wherein Ar is phenyl, M is sodium and Y is bromide.

* * * * *